United States Patent
Nagata et al.

(10) Patent No.: US 11,692,999 B2
(45) Date of Patent: Jul. 4, 2023

(54) METHOD OF SCREENING ATP11C OR CDC50A INHIBITOR

(71) Applicant: KYOTO UNIVERSITY, Kyoto (JP)

(72) Inventors: Shigekazu Nagata, Suita (JP); Katsumori Segawa, Suita (JP)

(73) Assignee: KYOTO UNIVERSITY, Kyoto (JP)

( * ) Notice: Subject to any disclaimer, the term of this patent is extended or adjusted under 35 U.S.C. 154(b) by 69 days.

(21) Appl. No.: 17/350,366

(22) Filed: Jun. 17, 2021

(65) Prior Publication Data
US 2021/0311019 A1 Oct. 7, 2021

Related U.S. Application Data

(62) Division of application No. 16/364,813, filed on Mar. 26, 2019, now Pat. No. 11,073,510, which is a division of application No. 15/301,762, filed as application No. PCT/JP2015/060817 on Apr. 7, 2015, now Pat. No. 10,295,528.

(60) Provisional application No. 61/978,415, filed on Apr. 11, 2014, provisional application No. 61/976,651, filed on Apr. 8, 2014.

(51) Int. Cl.
*G01N 33/50* (2006.01)
*A61P 35/00* (2006.01)

(52) U.S. Cl.
CPC ... *G01N 33/502* (2013.01); *G01N 2333/4703* (2013.01); *G01N 2333/914* (2013.01)

(58) Field of Classification Search
CPC ......... G01N 33/502; G01N 2333/4703; G01N 2333/914; A61P 35/00; A61P 43/00
See application file for complete search history.

(56) References Cited

U.S. PATENT DOCUMENTS

| | | |
|---|---|---|
| 2002/0137905 A1 | 9/2002 | Sims et al. |
| 2006/0233806 A1 | 10/2006 | Nagata |
| 2015/0079599 A1 | 3/2015 | Nagata et al. |
| 2015/0301024 A1 | 10/2015 | Nagata et al. |

FOREIGN PATENT DOCUMENTS

| | | |
|---|---|---|
| JP | 2003-155251 | 5/2003 |
| WO | 2012/029855 | 3/2012 |
| WO | 2013/157652 | 10/2013 |
| WO | 2014/077279 | 5/2014 |

OTHER PUBLICATIONS

Miyanishi M. et al., "Identification of Tim4 as a phosphatidyiserine receptor", Nature, Nov. 15, 2007, vol. 450, pp. 435-439. (Year: 2007).
Extended Search Report dated Jul. 31, 2017 in corresponding European patent application No. 15776310.3.
Database Biosis [Online] Biosciences Information Service, Philadephia, PA, US; Nov. 2013 (Nov. 2013), Lucy Coupland et al.: "Anemia, Shortened Erythrocyte Lifespan and Stomatocytosis In a Flippase Mutant Mouse Strain", XP002772240, vol. 122, No. 21, p. 2183.
Bevers E.M. et al.: "Phospholipid scramblase: An update", Febs Letters, Elsevier, Amsterdam, NL, vol. 584, No. 13, Jul. 2, 2000, pp. 2724-2730, XP027118854.
Database Biosis [Online] Biosciences Information Service, Philadelphia, PA, US; Dec. 2015 (Dec. 2015), Arashiki Nobuto et al.: "ATP11C Encodes a Major Flippase in Human Erythrocyte and Its Genetic Defect Causes Congenital Non-Spherocytic Hemolytic Anemia", XP002772242, vol. 126, No. 23.
Hiroyuki Takatsu et al.: "Phospholipid Flippase Activities and Substrate Specificities of Human Type IV p-type ATPases Locialized to the Plasma Membrane", Journal of Biological Chemistry, vol. 289, No. 48, Nov. 28, 2014, p. 33543-33556, XP055391710.
Segawa Katsumori et al.: "An Apoptotic 'Eat Me' Signal: Phosphatidyiserine Exposure", Trends in Cell Biology, vol. 25, No. 11, Nov. 2015, pp. 639-650, XP029321465.
International Search Report dated Jun. 23, 2015 in corresponding International (PCT) Application No. PCT/JP2015/060817.
International Preliminary Report on Patentability dated Oct. 12, 2016 in corresponding International (PCT) Application No. PCT/JP2015/060817.
P.A. Leventis, et al., "The Disuibution and Function of Phosphatidylserine in Cellular Membranes", Annu. Rev. Biophys. vol. 39, (2010), pp. 407-427.
B. Lentz, "Exposure of platelet membrane phosphatidyiserine regulates blood coagulation", Progress in Lipid Research vol. 42, (2003), pp. 423-438.
S. Nagata, et al., "Autoimmunity and the Clearance of Dead Cells", Cell, vol. 140, (2010), pp. 619-630.
J. Suzuki, et al., "Xk-Related Protein 8 and CED-8 Promote Phosphatidyiserine Exposure in Apoptotic Cells", Science , vol. 341, (2013), pp. 403-406.
J. Suzuki, et al., "Calcium-dependent phospholipid scrambling by TMEM16F", Nature, vol. 468, (2010), pp. 834-838.
P. Williamson, et al., "Transbilayer Phospholipid Movements in ABCA1-Deficient Cells", PLoS ONE, (2007), pp. e729.
K. Tanaka, et al., "Functions of phospholipid flippases" J. Biochem. vol. 149 No. 2, (2011), pp. 131-143.
T. Pomorski, et al., "Drs2p-related P-type ATPases Dnf1p and Dnf2p Are Required for Phospholipid Translocation across the Yeast Plasma Membrane and Serve a Role in Endocytosis", Molecular Biology of the Cell, vol. 14, (2003), pp. 1240-1254.
X. Tang, et al., "A subfamily of P-type ATPases with aminophoshlipid transporting activity", Science, vol. 272, (1996), pp. 1495-1497.
O. M. Siggs, et al., "X-linked cholestasis in mouse due to mutations of the P4-ATPase ATP11c", PNAS, vol. 108, No. 19, (2011), pp. 7890-7895.

(Continued)

*Primary Examiner* — Satyendra K Singh
(74) *Attorney, Agent, or Firm* — Wenderoth, Lind & Ponack, L.L.P.

(57) ABSTRACT

The present invention relates to a method for screening an inhibitor of ATP11C or CDC50A, comprising determining (a) exposure of phosphatidylserine on cell surface, (b) engulfment of cells by macrophages, or (c) cleavage of ATP11C by caspase. The present invention also relates to a method for inducing engulfment of cells by macrophages, comprising inhibiting ATP11C or CDC50A.

3 Claims, 35 Drawing Sheets

Specification includes a Sequence Listing.

(56) References Cited

OTHER PUBLICATIONS

M. Yabas, et al., "ATP11c is critical for phosphatidyiserine internalization and B lymphocyte differentiation", National Institute of Health, vol. 12, No. 5, (2011), pp. 441-449.

V. A. van der Mark, et al., "P4 ATPases: Flippases in Health and Disease", International Journal of Molecular Sciences, vol. 14, (2013), pp. 7897-7922.

T. T. Sebastian, et al., Phospholipid flippases: Building asymmetric membranes and transport vesicles, Biochimica Biophysica Acta, vol. 1821, (2012), pp. 1068-1077.

B. Verhoven, et al., "Mechanisms of Phosphatidyiserine Exposure, A Phagocyte Recognition Signal, on Apoptotic T Lymphocytes", J. Exp. Med, vol. 182, (1995), pp. 1597-1601.

D. L. Bratton, et al., "Apperance of Phosphatidyiserine on Apoptotic Cells Requires Calcium-mediated Nonspecific Flip-Flop and Is Enhanced by Loss of the Aminophospholipid Translocase", Journal of Biology Chemishy, vol. 272, No. 42, (1997), pp. 26159-26165.

M. Kotecki, et al., "Isolation and Characterization of a Near-Haploid Human Cell Line", Experimental Cell Research, vol. 252, (1999), pp. 273-280.

J. E. Carette, et al., "Global gene disruption in human cells to assign genes to phenotypes by deep sequencing", Nature Biotechnology, vol. 29, No. 6, (2011), pp. 542-546.

J. A. Coleman, et al., "Mammalian P4-ATPases and ABC transporters and their role in phospholipid transport", Biochimica et Biophysica Acta, vol. 1831, (2013), pp. 555-574.

L. Cong, et al., "Multiplex Genome Engineering Using CRISPR/Cas Systems", Science, vol. 339, (2013), pp. 819-823.

K. Segawa, et al., Constitutive exposure of phosphatidyiserine on viable cells, Proceedings of the National Academy of Sciences of the United States of America, vol. 108, (2011), pp. 19246-19251.

R. Hanayama, et al., "Identification of a factor that links apoptotic cells to phagocytes", Nature, vol. 417, (2002), pp. 182-187.

H. M. Seitz, et al., "Macrophages and Dendritic Cells Use Different Axl/Mertk/Tyro3 Receptors in Clearance of Apoptotic Cells", Journal of Immunology, vol. 178, (2007), pp. 5635-5642.

M. Overholtzer, et al., "A Nonapoptotic Cell Death Process, Entosis, that Occurs by Cell-in-Cell Invasion", Cell, vol. 131, (2007), pp. 966-979.

M. G. Palmgren, et al., "P-Type ATPases", Annu. Rev. Biophys. vol. 40, (2011), pp. 243-266.

M. Auland, et al., "Reconstitution of ATP-dependent aminophospholipid translocation in proteoliposomes", Proc. Natl. Acad. Sci. USA, vol. 91, (1994), pp. 10938-10942.

M. Darland-Ransom, et al., "Role of C. elegans TAT-1 Protein in Maintaining Plasma Membrane Phosphatidyiserine Asymmetry", Science, vol. 320, (2008), pp. 528-531.

U. Kato, et al., "Role for Phospholipid Flippase Complex of ATP8A1 and CDC50A Proteins in Cell Migration", Journal of Biological Chemistry, vol. 288, (2013), pp. 4922-4934.

A. Siegmund, et al., "Loss of Drs2p Does Not Abolish Transfer of Fluorescence-labeled Phospolipids across the Plasma Membrane of Saccharomyces cerevisiae", Journal of Biological Chemisty, vol. 273, No. 51, (1998), pp. 34399-34405.

U. Marx, et al., "Rapid transbilayer movement of fluorescent phospholipid analogues in the plasma membrane of endocytosis-deficient yeast cells does not require the Drs2 protein", Eur. J. Biochem. vol. 263, (1999), pp. 254-263.

B. Chen, et al., "Endocytic Sorting and Recycling Require Membrane Phosphatidyiserine Asymmetry Maintained by TAT-1/CHAT-1", PLoS Genetics, vol. 6, No. 12, (2010), pp. e1001235.

A.-F. Ruaud, et al., "The C. elegans P4-ATPase TAT-1 Regulates Lysosome Biogenesis and Endocytosis", Traffic, vol. 10, (2009), pp. 88-100.

L. M. van der Velden, et al., "Heteromeric Interactions Required for Abundance and Subcellular Localization of Human CDC50 Proteins and Class 1 P 4-atpATPases", Journal of Biological Chemistry, vol. 285, No. 51, (2010), pp. 40088-40096.

G. Lenoir, et al., Cdc50p Plays a Vital Role in the ATPase Reaction Cycle of the Putative Aminophospholipid Transporter Drs2p, Journal Biological Chemistry, vol. 284, No. 27, (2009), pp. 17956-17967.

A. Zachowski, "Phospholipids in animal eukaryotic membranes: transverse asymmetry and movement", Biochem. J., vol. 294, (1993), pp. 1-14.

J. I. Elliott, et al., "Membrane phosphatidyiserine disuibution as a non-apoptotic signalling mechanism in lymphocytes", Nature Cell Biology, vol. 7, No. 8, (2005), pp. 808-816.

D. L. Daleke, et al., "Identification and purification of aminophospholipid flippases", Biochimica Biophysica Acta, vol. 1486, (2000), pp. 108-127.

P. A. Oldenborg, et al., "Role of CD47 as a Marker of Self on Red Blood Cells", Science, vol. 288, (2000), pp. 2051-2054.

J. J. Neher, et al., "Inhibition of Microglial Phagocytosis Is Sufficient To Prevent Inflammatory Neuronal Death", The Journal of Immunolology, vol. 186, (2011), pp. 4973-4983.

G. C. Brown, et al., "Eaten alive! Cell death by primary phagocytosis: 'phagoptosis'", Trends in Biochem Sciences, vol. 37, No. 8, (2012), pp. 325-332.

C. Toyoshima, et al., "Structural Basis of Ion Pumping By CA2+ -ATPase of the Sarcoplasmic Reticulum", Annu Rev Biochem, vol. 73, (2004), pp. 269-292.

Q. Lu, et al., "Tyro-3 family receptors are essential regulators of mammalian spermatogenesis", Nature, vol. 398, (1999), pp. 723-728.

R. Watanabe-Fukunaga, et al., "Pillars Article: Lymphoproliferation Disorder in Mice Explained by Defects in Fas Antigen that Mediates Apoptosis", Nature, vol. 356, (1992), pp. 314-317.

H. Sakahira, et al., "Cleavage of CAD inhibitor in CAD activation and DNA degradation during apoptosis", Nature, vol. 391, (1998), pp. 96-99.

T. Kitamura, "New experimental approaches in retrovims-mediated expression screening" International Journal of Hematology, vol. 67, (1998), pp. 351-359.

T. Shiraishi, et al., "Increased cytotoxicity of soluble Fas ligand by fusing isoleucine zipper motif", Biochemical and Biophysical Research Communications, vol. 322, (2004), pp. 197-202.

J. Carette, et al., "Haploid Genetic Screens in Human Cells Identify Host Factors Used by Pathogens", Science, vol. 326, (2009), pp. 1231-1235.

M. A. Nesbit, et al., "X-linked hypoparathyroidism region on Xq27 is evolutionarily conserved with regions on 3q26 and 13q34 and contains a novel P-type ATPase", Genomics, vol. 84, (2004), pp. 1060-1070.

R. Higuchi, "Recombinant PCR ", protocols: A guide to methods and applications, Academic Press, San Diego, CA, (1990), pp. 177-188.

R. Fukunaga, et al., Purification and Characterization of the Receptor for Murine Granulocyte Colony-stimulating factor, Jornal of Biology Chemistry, vol. 265, No. 23, (1990), pp. 14008-14015.

M. Miksa, et al., A novel method to determine the engulfment of apoptotic cells by macrophages using pHrodo succinimidyl ester, Journal of Immunological Methods, vol. 342, (2009), pp. 71-77.

S. Toda, et al., "Two-step engulfment of apoptotic cells", Molecular and Cellular Biology, vol. 32, (2012), pp. 118-125.

H. Takatsu, et al., ATP9B, a P4-ATPase (a putative aminophospholipid translocase), localizes to the trans-Golgi network in a CDC50 protein-independent manner, Jouranl of Biological Chemistry, vol. 286, No. 2, (2011), pp. 38159-38167.

Folmer DE, et al., "P4 ATPases-Lipid flippases and their role in disease", Biochimica et Biophysica Acta, (2009), pp. 628-635.

Segawa K., et al., "Caspase-mediated cleavage of phospholipid flippase for apoptotic phosphatidyiserine exposure". Science, vol. 344, No. 6188, (2014), pp. 1164-1168.

Fischer K. et al., "Antigen recognition induces phosphatidyiserine exposure on the cell surface of human CD8+T cells", BLOOD, 2006, vol. 108, No. 13, pp. 4094-4101. (Year: 2006).

Zwaal R.F.A. et al., "Scott syndrome, a bleeding disorder caused by defective scrambling of membrane phospholipids", Biochimica et Biophysica Acta, 2004, vol. 1636, pp. 119-128 (Year: 2004).

(56) References Cited

OTHER PUBLICATIONS

Kagan V.E. et al., "A Role for Oxidative Stress in Apoptosis: Oxidation and Externalization of Phosphatidyiserine Is Required for Macrophage Clearance of Cells Undergoing Fas-Mediated Apoptosis", the Journal of Immunology, 2002, vol. 169, pp. 487-499.

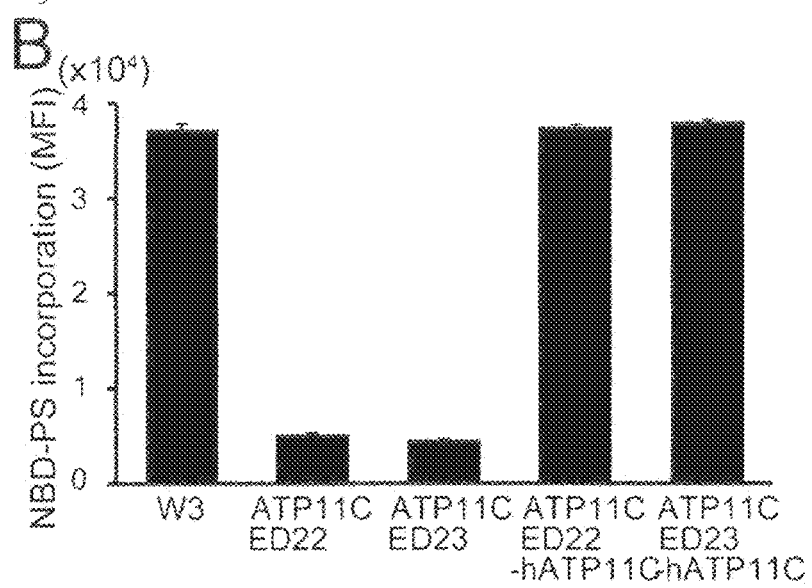

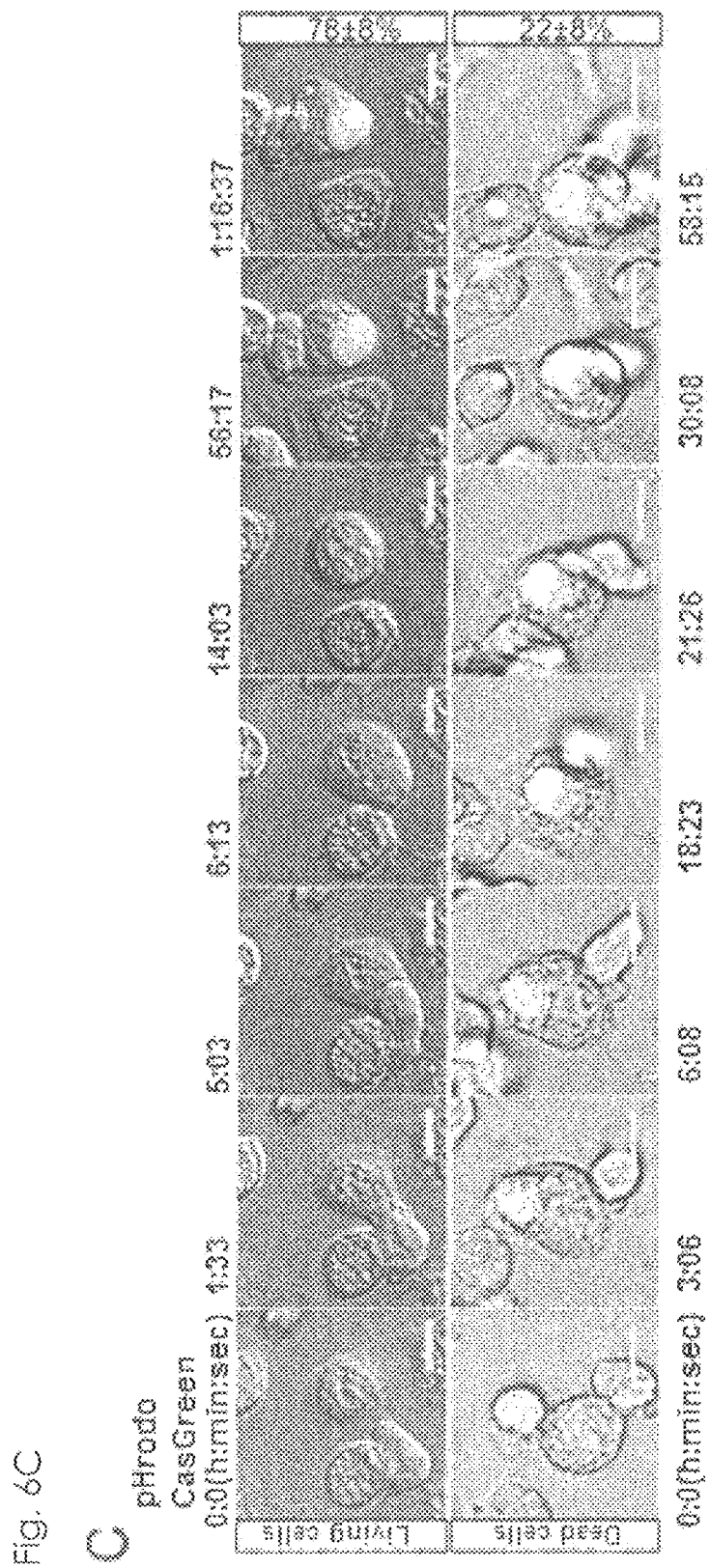

Fig. 7A
A
1. Reverse transcription
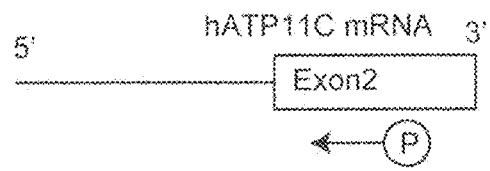
2. Ligation and PCR
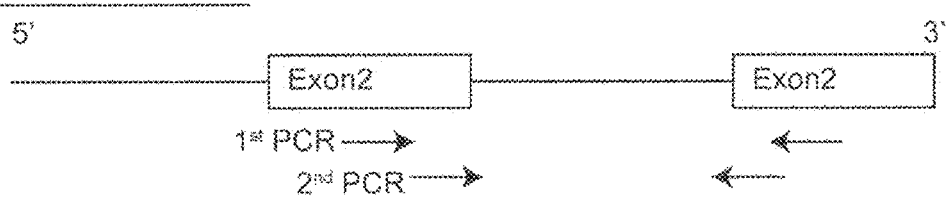
Fig. 7B
B
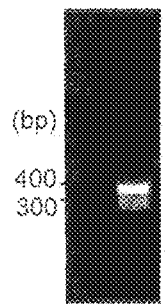
Fig. 7C
C
GAGAGCCGAGGGGGGCAGGCGGCGAGCGGGTGGCCGGGCGCCCGGCTCGCTGCTCCGCTTGGCGCCGCGGCCC
ACGGCGCAGTGTGTTTTGTGGACGGCGCCTTCCCAGACAGCCGGTAGAGCCCAGCTCAGCGCCCGGCAGCCTTC
GACGCGATGTCCGGCGGAGCTTGAATCGTTTTTGTGCTG ---
　　　　　M F R R S L N R F C A
　　　　　　　　　　　　　　　　　Exon2

METHOD OF SCREENING ATP11C OR CDC50A INHIBITOR

TECHNICAL FIELD

The present invention relates to a method for screening an inhibitor of ATP11C or CDC50A. The present invention also relates to a method for inducing engulfment of cells by macrophages.

BACKGROUND ART

Plasma membrane in eukaryotes is composed of phospholipid bilayer where phospholipids are distributed asymmetrically. Phosphatidylserine having an amino group is located in the inside part of the membrane (the inner leaflet) and not in the outside part of the membrane (the outer leaflet). The asymmetrical distribution of phosphatidylserine is considered to be maintained by the action of an enzyme flippase which transports aminophospholipids toward cytoplasmic side of plasma membrane. In contrast, in apoptotic cells, the asymmetrical distribution of phosphatidylserine is disrupted, and phosphatidylserine is no longer confined to the inner leaflet, but is allowed to be exposed on the cell surface. Phagocytes are considered to recognize phosphatidylserine exposed on apoptotic cells and engulf the cells specifically rather than viable cells. However, molecular mechanism is unknown responsible for the asymmetrical membrane distribution of phosphatidylserine in viable cells and the surface exposure of phosphatidylserine in apoptotic cells. Also, it has not been known whether apoptotic cells can induce their engulfment by phagocytes solely by the surface exposure of phosphatidylserine.

CITATION LIST

Patent Documents

Patent Document 1: WO 2012/029855 (incorporated herein by reference)
Patent Document 2: WO 2013/157652 (incorporated herein by reference)
Patent Document 3: WO 2014/077279 (incorporated herein by reference)

SUMMARY

The inventors have studied the mechanism responsible for plasma membrane distribution of phosphatidylserine in viable cells or apoptotic cells, and effects of the mechanism on phagocytosis. Finally, the inventors have found that ATP11C and CDC50A take part in the mechanism of exposing phosphatidylserine on surface of apoptotic cells, and that phosphatidylserine is exposed upon inactivation of ATP11C by its cleavage by caspase.

The present invention provides a method for screening an inhibitor of ATP11C or CDC50A, comprising determining (a) exposure of phosphatidylserine on cell surface, (b) engulfment of cells by macrophages, or (c) cleavage of ATP11C by caspase.

The present invention provides a method for inducing engulfment of cells by macrophages, comprising inhibiting ATP11C or CDC50A.

BRIEF DESCRIPTION OF DRAWINGS

FIG. 3B Cleavage of ATP11C by caspase (B). W3, ATP11C$^{ED2}$- and ATP11C$^{ED23}$, and their hATP11C-transformants were incubated for 15 min with NBD-PS. Incorporated NBD-PS is expressed by MFI (n=3).

FIG. 6C Engulfment of PtdSer-exposing viable cells (C). pHrodo-labeled CDC50A$^{ED29}$ were incubated with thio-pMacs in the presence of CellEvent™ caspase 3/7 Green (Cas/green). Images for pHrodo, CellEvent™, and DIC were captured every 1.5 min. Engulfment of Cas/Green-negative (living) and -positive (dead) cells were followed for at least 130 events in 30 different fields of 3 independent experiments. The percentage of dead or living cell engulfment was determined relative to total engulfment, and shown at right. Scale bar, 10 μm.

FIG. 7A The transcription initiation site for hATP11C determined by 5'-RACE-PCR (A). The cDNA encompassing the 5'-region of hATP11C mRNA was prepared by reverse-transcribing mRNA with a phosphorylated primer in exon 2. The cDNA was then ligated, and used as a template for the nested PCR. Primers used for the nested PCR (1st and 2nd PCR) are indicated by arrows.

FIG. 7B The transcription initiation site for hATP11C determined by 5'-RACE-PCR (B). 5'-RACE-PCR products are shown.

FIG. 7C The transcription initiation site for hATP1C determined by 5'-RACE-PCR (C). Sequence at the 5' end of hATP11C determined by 5'-RACE-PCR. The 400-bp DNA fragment in FIG. 7B was cloned into the pGEM-T easy vector, and the DNA sequence was determined. The putative transcription initiation sites are indicated by arrows. Exon 2 and the initiation codon are indicated by boxes.

DESCRIPTION OF EMBODIMENTS

Figure 1A:
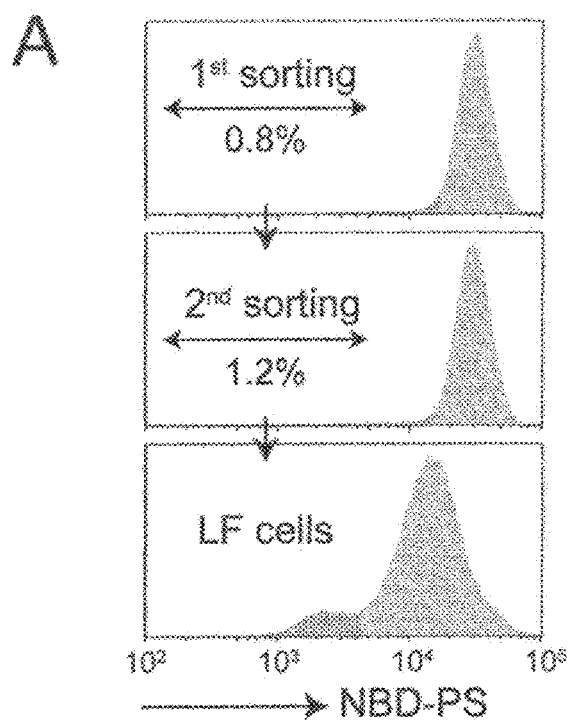
FIG. 1A Genetic screening using haploid cells (A). KBM7 exhaustively transfected with retrovirus was incubated with NBD-PS, and analyzed by FACS. Approximately 1.0% of the cells with a reduced ability to incorporate NBD-PS were collected, expanded, and sorted again, resulting in low flipping (LF) cells.

ATP11C is a member of P4-ATPase family and CDC50A is a β-subunit of members of the P4-ATPase family. ATP11C is responsible for distribution of phosphatidylserine (PtdSer) in plasma membrane by transporting PtdSer toward the inner leaflet. CDC50A controls, as a subunit of ATP11C, flippase activity of ATP11C. Nucleotide sequences of ATP11C and CDC50A and amino acid sequences of ATP11C and CDC50A have been known. For example, cDNA sequences of hATP11C and hCDC50A are disclosed under NM_018247.3 and XM_005262405.1, respectively, in NCBI database.

Candidates for ATP11C or CDC50A inhibitors may be natural products or synthetic products, and may include low molecular weight compounds, proteins, nucleic acid molecules, peptides, antibodies, or extracts or supernatants of cultures of microorganisms or plant or animal cells. Candidates may be provided in the form of a library, for example, a library of low molecular weight compounds, peptides or antibodies. Candidates are typically added to a solution containing cells, membrane fractions of cells, or artificial lipid bilayers (for example, a medium of cell culture).

Cells expressing ATP11C are herein intended to mean cells expressing ATP11C inherently, or cells transfected with gene encoding ATP11C to express ATP11C. Similarly, cells expressing CDC50A may be cells expressing CDC50A inherently, or cells transfected with gene encoding CDC50A to express CDC50A. Cells include, but not limited to, cells from human, monkey, murine and rabbit. For example, KBM7, Jurkat, W3 or Ba/F3 may be used in the present invention. Methods for preparing cells expressing ATP11C and/or CDC50A by transfection of gene encoding ATP11C and/or CDC50A are conventionally known (Molecular Cloning: A Laboratory Manual (Fourth Edition), Cold Spring Harbor Laboratory Press).

Inhibitors of ATP11C or CDC50A are herein intended to mean substances that inhibit flippase activity of ATP11C in cells or animals and, therefore, include substances affecting the function of ATP11C or CDC50A directly or indirectly, and substances inhibiting expression of ATP11C or CDC50A. Substances inhibiting expression of ATP11C or CDC50A include substances inhibiting synthesis of mRNA from gene encoding ATP11C or CDC50A, and substances inhibiting expression of ATP11C or CDC50A protein. Thus, an inhibitor of ATP11C or CDC50A may be a substance affecting regulatory sequence such as promotor or enhancer in ATP11C- or CDC50A-encoding gene, or antisense oligonucleotide (DNA or RNA), siRNA, miRNA or ribozyme synthesized for sequence of ATP11C- or CDC50A-encoding gene, or a vector expressing the antisense oligonucleotide, siRNA, miRNA or ribozyme. The inhibitor of ATP11C or CDC50A may also be Crispr/Cas system targeting ATP11C- or CDC50A-encoding gene. Since ATP11C is inactivated upon caspase-mediated cleavage, an inhibitor of ATP11C may be a substance promoting caspase-mediated ATP11C cleavage.

In one embodiment, the method of the present invention comprises determining flippase activity of ATP11C. ATP11C is responsible for distribution of PtdSer in plasma membrane by transporting PtdSer toward the inner leaflet. Therefore, flippase activity of ATP11C may be determined by analysis of PtdSer distribution in plasma membrane.

When a candidate shifts PtdSer distribution toward the outer leaflet (or increases PtdSer exposure) compared to control, the candidate is selected as an inhibitor of ATP11C. The "control" refers to the amount of PtdSer in the outer leaflet in the absence of the candidate.

PtdSer distribution in plasma membrane may be analyzed by determining PtdSer exposed on cell surface through detection of a substance capable of binding to PtdSer, such as Annexin V or MFG-E8 (lactadherin), bound to the exposed PtdSer. For example, cells are treated with fluorescently labeled Annexin V, and then the amount of Annexin V bound to cell surface is determined.

Analysis of PtdSer distribution in plasma membrane may alternatively be based on blood coagulation reaction. For example, cells may be treated with a candidate in the presence of substance(s) required to blood coagulation (for example, factor Xa, factor Va, or prothrombin) in a medium. Then, synthesis of thrombin in the medium may be determined. Synthesis of fibrin may be determined, if fibrinogen is included in the medium.

For analyzing PtdSer distribution in plasma membrane, fluorescently labeled PtdSer may be utilized. NBD, Top-Fluor or other fluorescent dyes may be used for this purpose. For example, cells may be cultured in a medium containing fluorescently labeled PtdSer so that the PtdSer is incorporated into the outer leaflet of the cells. When ATP11C functions as flippase, the incorporated PtdSer is transported toward the inner leaflet. If a candidate inhibits ATP11C, exposure of PtdSer on cell surface in the presence of the candidate increases compared to that in the absence of the candidate. Thus, after cells expressing ATP11C are treated with a candidate in the presence of fluorescently labeled PtdSer, the cells may be treated with BSA to remove fluorescently labeled PtdSer exposed on cell surface and subjected to flow cytometry for determination of incorporated PtdSer in cells.

PtdSer exposure on cell surface of cells induces engulfment of the cells by macrophages. Therefore, analysis of flippase activity of ATP11C may alternatively be based on cell engulfment by macrophages.

For determining cell engulfment by macrophages, peritoneal macrophages may be obtained from mice intraperitoneally injected with thioglycollate and grown in plates. Then, pHrodo™-stained cells such as W3 may be added to the plates. Several tens of minutes or several hours later, the macrophages may be subjected to flow cytometry or directly examined microscopically.

In one embodiment, the method of the present invention comprises determining caspase-mediated ATP11C cleavage. Caspase-mediated ATP11C cleavage may be determined by Western blotting. For example, proteins may be separated from lysate of cells or membrane fractions thereof by SDS-PAGE, transferred to membrane, and probed with anti-ATP11C antibody, thereby determining size of ATP11C.

It is also possible to determine caspase-mediated ATP11C cleavage without using cells. For example, a candidate of ATP11C inhibitor may be applied to artificial lipid bilayer containing ATP11C incorporated therein in the presence of caspase. Then, caspase-mediated ATP11C cleavage in the lipid bilayer may be determined.

ATP11C and CDC50A take part in the mechanism of exposing PtdSer on surface of apoptotic cells. Therefore, The method of the present invention is useful for development of drugs for treatment or prophylaxis of cancers or apoptosis-related diseases including autoimmune diseases.

PtdSer exposure on cell surface induces engulfment of the cells by macrophages. Therefore, the engulfment can be induced by inhibition of ATP11C or CDC50A. ATP11C or CDC50A may be inhibited by an inhibitor of ATP11C or CDC50A selected by the screening method of the present invention. ATP11C or CDC50A may alternatively be inhibited by Crispr/Cas system targeting ATP11C- or CDC50A-encoding gene, as described in the Example below.

Cancers or apoptosis-related diseases, which are characterized by abnormal cell proliferation, may be treated or prevented by induction of engulfment of the cells by macrophages. Therefore, in one embodiment of the present invention, engulfment of cells by macrophages is engulfment of cancer cells. In one embodiment of the present invention, an inhibitor of ATP11C or CDC50A is administered to a subject in need of the treatment or prophylaxis.

Further, the present invention provides a pharmaceutical composition for inducing engulfment of cells by macrophages comprising an inhibitor of ATP11C or CDC50A. The present invention also provides use of an inhibitor of ATP11C or CDC50A for the manufacture of a medicament for inducing engulfment of cells by macrophages.

The present invention is illustrated by the following Example which is not meant to limit the scope of the invention.

Example 1

1. Materials and Methods
Mice, Cell Lines, Plasmids, Recombinant Proteins, Antibodies, and Reagents C57BL/6J and BALB/c nude mice were purchased from Japan Clea. MerTK$^{-/-}$ mice (41) were purchased from the Jackson Laboratory. All mouse studies were approved by the Ethics Review Committee for Animal Experimentation of the Graduate School of Medicine, Kyoto University.

Human KBM7 cell line (16) was provided by Dr. Brent H. Cochran (Tufts University School of Medicine) and maintained in Iscove's Modified Dulbecco's Medium (IMDM) containing 10% FCS. W3 cells are transformants of mouse T-cell lymphoma cells (WR19L) that express mouse (m)Fas (42), and W3-Ildm cells are WR19L cells expressing Fas and a caspase-resistant form of the inhibitor of caspase-activated DNase (ICAD) (43). W3 cells, W3-Ildm cells and human Jurkat cells were cultured in RPMI1640 containing 10% FCS. W3-Ildm transformants expressing a constitutively active form of mTMEM16F (W3-D430G-L) were described previously (20). HEK293T cells were cultured in DMEM containing 10% FCS. For the analysis of phosphatidylserine (PtdSer) exposure and some other experiments, FCS was centrifuged at 100,000×g overnight at 4° C., followed by filtration using 0.22-mm membranes (Millipore) to remove microvesicles or debris.

The gene-trap constructs (pGT-GFP, pGT-GFP+1, and pGT-GFP+2) were described previously (17). The retrovirus vector pMXs-puro (44) and packaging plasmid pGag-pol-IRES-bsr were from Dr. Toshio Kitamura (Institute of Medical Science, University of Tokyo). The plasmid pCMV-VSV-G was provided by Dr. Hiroyuki Miyoshi (Riken Bioresource Center, Riken). pAdVAntage™, pX260, and pX330 (19) were purchased from Life Technologies (Invitrogen) and Addgene, respectively. Recombinant leucine-zippered human FasL (FasL) (45) and the D89E mutant of mMFG-E8 (21) were produced in COS7 and HEK293T cells, respectively, and purified. The Cy5-labeled Annexin V and FITC-labeled bovine MFG-E8 (BLAC-FITC) were purchased from Biovision, and Hematologic Technologies, respectively. pHrodo™ succinimidyl ester (pHrodo) and CellEvent™ Caspase-3/7 Green were purchased from Life Technologies. 1-oleoyl-2-{6-[(7-nitro-2-1,3-benzoxadiazol-4-yl)amino]hexanoyl}-sn-glycero-3-phosphoserine (NBD-PS), 1-oleoyl-2-{6-[(7-nitro-2-1,3-benzoxadiazol-4-yl)amino]hexanoyl}-sn-glycero-3-phosphoethanolamine (NBD-PE), and 1-oleoyl-2-{6-[(7-nitro-2-1,3-benzoxadiazol-4-yl)amino]hexanoyl}-sn-glycero-3-phosphocholine (NBD-PC) were purchased from Avanti Polar Lipids.

Rabbit antibodies (Ab) against mATP11C were custom-prepared at the Protein Purity Co. In brief, a peptide, PYNDEPWYNQKTQKERET (amino acids 317-334) (SEQ ID NO: 1) with an extra cysteine residue added at the N-terminus, was conjugated to keyhole limpet hemocyanin with m-maleimidobenzoyl-N-hydroxysuccinimide ester (Pierce), and used to immunize rabbits. The antibodies were affinity-purified from the serum using AF amino-Toyopearl™ beads (AF-Amino-650, Tosoh Co) bound to the peptide. Rat anti-mouse Fas mAb (clone OB-22) was prepared by the standard protocol in our laboratory.

Haploid Genetic Screen

The haploid genetic screen was performed essentially as described (17, 46). In brief, to produce the gene trap virus, HEK293T cells ($2.4 \times 10^7$ cells) were co-transfected using Fugene6 (Promega) with a mixture (36 µg) of pGT-GFP, pGT-GFP+1, and pGT-GFP+2, combined with 8.4 µg pAdvantage, 9.0 µg pCMV-VSV-G, and 9.6 µg pGag-pol-IRES-bsr, and incubated for 48 h. The virus in the supernatant was concentrated by centrifugation at 6,000×g for 16 h. KBM7 cells ($1 \times 10^8$) were seeded at $1.5 \times 10^6$ cells per well in 24-well culture dishes (Corning), and infected with the concentrated virus using spin-infection at 700×g for 45 min in the presence of 8 µg/ml polybrene. The infected cells, where the efficiency of viral incorporation was approximately 80%, were expanded for 4 days and used for screening.

The cells that lost the ability to transport aminophospholipids across the plasma membrane were enriched by repeating the FACS sorting twice. In brief, $6 \times 10^7$ mutagenized KBM7 cells were washed with PBS, and incubated at room temperature for 40 min with 1.5 µM NBD-PS in Hank's balanced salt solution (HBSS) containing 2 mM $CaCl_2$ and 1 mM $MgCl_2$. The cells were collected by centrifugation, and suspended in HBSS containing 5 mg/ml fatty-acid-free BSA (Sigma-Aldrich) to remove NBD-PS on the cell surface. The cells were subjected to flow cytometry at 4° C. using the FACSAria II system (BD Biosciences), and approximately 1% of the cells, which exhibited less efficient NBD-PS incorporation, were collected. The sorted cells were grown for 1-2 weeks in IMDM containing 10% FCS, and subjected to a second sorting as described above. The resultant cells exhibiting defective NBD-PS incorporation were designated as Low-Flipping or LF cells.

Mapping of Gene-Trap Insertion Sites

Host sequences flanking the proviral insertion were identified by inverse PCR, followed by deep sequencing as described (17, 46). In brief, genomic DNA was isolated from $2 \times 10^6$ LF cells using the QIAamp DNA Mini Kit (Qiagen), and 4 µg DNA was digested with NlaIII. The digested DNA was purified using the Wizard SV Gel and PCR clean-up column (Promega), and 1.0 µg DNA was ligated with T4 DNA ligase (Takara Bio) in a volume of 300 µl. The DNA was purified as above, and subjected to PCR using outward-facing primers complementary to the internal sequence in the gene trap vector (5'-AATGATACGGCGACCACCGAGATCTACACATCTGA TGGTTCTCTAGCTTGCC-3' (SEQ ID NO: 2) and 5'-CAAGCAGAAGACGGCATACGAGATACCCAGGTTA AGATCAAGGTC-3' (SEQ ID NO: 3); adapter sequences for deep sequencing are underlined). The PCR products were purified by the Wizard SV Gel and PCR clean-up column, and sequenced with a primer (5'-CTAGCTTGC-CAAACCTACAGGTGGGGTCTTTCA-3' (SEQ ID NO: 4)) on a MiSeq sequencer (Illumina).

The 45-bp sequences in the FASTQ data file were mapped to the human genome (UCSC human genome 19; hg19) using Burrows-Wheeler Aligner software. The criteria used by Carette et al. (17) were applied to identify unique insertion sites. That is, the sequences carrying mismatches in the 45-bp sequence were removed, and if several insertions aligned 1 or 2 base pairs apart, only 1 was retained. The proximity index for a given insertion was defined as the inverse value that was calculated from the average distance between the given insertion and the two neighboring upstream and downstream insertions.

Isolation of KBM7 Clones Carrying the Gene-Trap Mutations

To obtain clonal cell lines that carried gene-trap insertions, the LF cells were subjected to limiting dilution. Genomic DNA was isolated from each clone using the QIAamp DNA Mini Kit, digested with NlaIII, and purified using the Wizard SV Gel and PCR clean-up column. The DNA was ligated with T4 DNA ligase, purified as above, and subjected to PCR using outward-facing primers complementary to the internal sequence in the gene trap vector (5'-CTGCAGCATCGTTCTGTGTT-3' (SEQ ID NO: 5) and 5'-TCTCCAAATCTCGGTGGAAC-3' (SEQ ID NO: 6)). The amplified PCR products were directly sequenced using a DNA sequencer (ABI PRISM 3100 Genetic Analyzer, Life Technologies) with the primer (5'-CTCGGTGGAACCTC-CAAAT-3' (SEQ ID NO: 7)). Clones carrying mutations in ATP11C or CDC50A were designated ATP11C$^{GT}$ and CDC50A$^{GT}$, respectively.

Gene Editing

The CRISPR-Cas system (19) was used to edit the mCDC50A and ATP11C genes in W3 and W3-Ildm cells. Suitable target sequences in the mCDC50A (TMEM30A) (ID: MGI 106402) and mATP11C (ID: MGI 1859661) genes were designed using the CRISPR Design Tool at Zhang's Laboratory at UCSC (http://www.genome-engineering.org/crispr/?page_id=41). Complementary oligonucleotides (5'-AAAC CATCGGCCTCATCTTCATCCCCATCGGCATGT-3' (SEQ ID NO: 8) and 5'-TAAAAC ATGCCGATGGGGATGAAGATGAGGCCGATG-3' (SEQ ID NO: 9) for CDC50A, and 5'-CACCGTCAC-CAAACGGTTGAGGGTC-3' (SEQ ID NO: 10) and 5'-AAACGACCCTCAACCGTTTGGTGAC-3' (SEQ ID NO: 11) for ATP11C, with target sequences for CDC50A and ATP11C underlined) were phosphorylated with T4 polynucleotide kinase (Takara Bio), heated at 95° C. for 5 min, left at room temperature for annealing, ligated into BbsI-digested pX260 (for CDC50A) or pX330 (for ATP11C) vectors, and used to transform E. coli. The pX plasmid DNA carrying the targeted sequences was introduced into W3 or W3-Ildm cells by electroporation using a Super Electroporator NEPA21 type II (NepaGene). After culturing for 3 days in RPMI containing 10% FCS, the cells were transfected again with the pX vectors.

To identify clones carrying mutations, the cells were subjected to limiting dilution 3 days after the second transfection, and the genomic DNA was prepared from individual clones using a QIAamp DNA Mini Kit. The DNA fragment flanking the CRISPR-target site was amplified by PCR using primers (CDC50A: 5'-CGTCTCCTAAAGACGCCCG-3' (SEQ ID NO: 12) and 5'-TCCACCCGACATTCTAGCTG-3' (SEQ ID NO: 13), and ATP11C: 5'-GCAGTGTGTTTTGTGGACGG-3' (SEQ ID NO: 14) and 5'-CCGGGTTTCCGCTAAAACGC-3' (SEQ ID NO: 15)), and directly sequenced using a DNA sequencer (ABI PRISM 3100 Genetic Analyzer). Gene editing at the CDC50A gene locus was observed in 6 of 96 clones, and 2 of them (CDC50A$^{ED29}$ and CDC50A$^{ED62}$) carried biallelic changes that resulted in frame-shifting indels. Gene editing at the ATP11C gene locus was observed in 9 of 34 clones, 4 of which were ATP11C-deficient clones carrying biallelic indels. Among them, 2 clones (ATP11C$^{ED22}$ and ATP11C$^{ED23}$) were used in this study.

5'-RACE-PCR

Amplification of 5'-cDNA ends was performed using a kit (5'-Full RACE Core Set; Takara Bio) according to the manufacturer's instructions. In brief, RNA was prepared from KBM7 cells with the RNeasy Mini Kit (Qiagen). The first-strand cDNA was synthesized using AMV (Avian Myeloblastosis Virus) Reverse Transcriptase with a 5'-phosphorylated primer (5'-CTTAGATGAGAC-3' (SEQ ID NO: 16)). After degrading RNA with RNase H, the synthesized first-strand cDNA was ligated with T4 RNA ligase, and used as a template for nested PCR. Nested PCR was carried out using primers as follows (for $1^{st}$ PCR; 5'-TGGCAATCATCCAGTTTCGG-3' (SEQ ID NO: 17) and 5'-ACACTGTGCGTGTGCCAAC-3' (SEQ ID NO: 18), for $2^{nd}$ PCR; 5'-CGGAAACAGAAGCTTACATTGC-3' (SEQ ID NO: 19) and 5'-TCGTTTCTCTTCTCCAGCAC-3' (SEQ ID NO: 20)). The PCR product was cloned in the pGEM-T easy vector, and DNA sequences were determined with a DNA sequencer (ABI PRISM 3100 Genetic Analyzer).

Transformation of Human and Mouse Cell Lines

The human CDC50A cDNA (NCBI: NM_018247.3) was prepared by RT-PCR with RNA from KBM7 cells. Since the native hATP11C cDNA (NCBI: XM_005262405.1) (47) produced low protein levels in mammalian cells, a sequence with enhanced mRNA stability and translational efficiency was custom ordered from GENEART (Regensburg, Germany). To generate the Mut1+2, 1+3, 2+3, or 1+2+3 mutants, hATP11C cDNA was mutated by recombinant PCR (48) using the following primers carrying the mutated nucleotides, with the sequence for the restriction enzyme site underlined: hATP11C (5'-CAT<u>TTAATTAA</u>GCCACCATGTTCAG-3' (SEQ ID NO: 21) and 5'-CC<u>AGGAATTC</u>CAGCACGTTGGACTC-3') (SEQ ID NO: 22); Mut1, 5'-CTGTCTGGCTCAGGCCGGCCACTTCCTGGGTCACG-3' (SEQ ID NO: 23) and 5'-CGTGACCCAGGAAGTGGCCGGCCTGAGCCAGACAG-3' (SEQ ID NO: 24); Mut2, 5'-GAAGTAGGTCAGTGTGCCAGCTGTCTGGCTCAGGC-3' (SEQ ID NO: 25) and 5'-GCCTGAGCCAGACAGCTGGCACACTGACCTACTTC-3' (SEQ ID NO: 26); and Mut3, 5'-CTCTGTGGCGCCGGCCACGGCGGCGGTGGTCTTGA-3' (SEQ ID NO: 27) and 5'-TCAAGACCAACGCCGCCGTGGCCGGCGCCACAGAG-3' (SEQ ID NO: 28). The authenticity of the cDNAs was confirmed by DNA sequencing.

KBM7 cells, W3 cells, W3-Ildm cells, Jurkat cells, and their derivatives were transformed using a retrovirus vector carrying the VSV-G envelope gene. The cDNAs were Flag- or GFP-tagged at the C-terminus, inserted into the pMXs-puro vector, and introduced into HEK293T cells using Fugene 6 (Promega), together with pGag-pol-IRES-bsr, pCMV-VSV-G, and pAdVAntage™. The produced retrovirus was concentrated by centrifugation and used to infect KBM7 cells, W3 cells, W3-Ildm cells, or Jurkat cells. The infected cells were cultured in the presence of puromycin at 0.8 µg/ml (for KBM7 cells) or 1 µg/ml (for W3 cells, W3-Ildm cells or Jurkat cells).

Induction of Apoptosis and Detection of Phosphatidylserine

To induce apoptosis, $1\times10^6$ W3-Ildm cells were treated with 33 units/ml FasL at 37° C. for 1-2 h, and the cell viability was determined by the WST-1 assay with 2-(4-iodophenyl)-3-(4-nitrophenyl)-5-(2,4-disulfophenyl)-2H-tetrazolium, monosodium salt (WST-1; Dojin Laboratories) and 1-methoxy-5-methylphenazinium methylsulfate, as described (20).

To detect PtdSer (phosphatidylserine) on the cell surface, cells were incubated at 25° C. for 5 min with 1-2,000-fold diluted Cy5-Annexin V or 800 ng/ml FITC-MFG-E8 in Annexin V-buffer (10 mM Hepes-KOH (pH 7.4), 140 mM NaCl, and 2.5 mM $CaCl_2$) or IMDM supplemented with 10% FCS, followed by incubation with 200 nM SYTOX® (Blue (Life Technologies Molecular Probes), and analyzed by a FACSAria II or FACSCanto II. For microscopic observation, $2\times10^5$ cells on 8-well Lab-Tek II chamber slides (Nalge Nunc) were incubated on ice for 15 min with 4 µg/ml FITC-conjugated MFG-E8 in staining buffer and observed by confocal fluorescence microscopy (FV1000-D; Olympus).

Caspase Treatment

The membrane fractions were prepared from cells expressing hATP11C-GFP or its mutants as described (49), and lysed in 20 mM Tris-HCl (pH 7.4), 140 mM NaCl, 1% Triton X-100, 10% glycerol, and 1 mM (p-aminophenyl) methanesulfonyl fluoride (APMSF). After removing insoluble materials by centrifugation, the membrane proteins (10 µg) were incubated at 37° C. for 1 h with 3 units of various recombinant human caspases (Biovision) in 100 µl of 50 mM Hepes-NaOH (pH 7.4), 5% glycerol, 5 mM DTT, 10 mM EDTA, 0.1 mM APMSF and 0.1% CHAPS, and analyzed by Western blotting.

Western Blotting

Cells or membrane fractions were lysed in RIPA buffer (50 mM HEPES-NaOH (pH 8.0) containing 1% NP-40, 0.1% SDS, 0.5% sodium deoxycholate, 150 mM NaCl, and a cocktail of protease inhibitors [cOmplete, Mini, EDTA-free, Roche Diagnostics]). After removing insoluble materials by centrifugation, the lysates were mixed 3:1 with 3×SDS sample buffer (200 mM Tris-HCl [pH 6.8], 10% SDS, 25% glycerol, 15% β-mercaptoethanol, and 0.05% bromophenol blue), and incubated at room temperature for 20 min. Proteins were separated by SDS-PAGE using a 7.5% or 10-20% gradient gel (Bio Craft), and transferred to a PVDF membrane (Millipore). The membranes were probed with mouse anti-GFP mAb, rabbit anti-active caspase-3 mAb, rabbit anti-hATP11C Ab, rabbit anti-α-tubulin mAb, or rat anti-mFas mAb, followed by incubation with HRP-conjugated goat anti-mouse Igs, goat anti-rabbit Igs or rabbit anti-rat Igs (Dako). The peroxidase activity was detected by the Western Lightning-ECL system (PerkinElmer).

In Vitro Phagocytosis Assay

To prepare thioglycollate-elicited peritoneal macrophages (thio-pMacs), female C57BL/6J mice at 7-12 weeks of age were injected intraperitoneally with 60 mg of thioglycollate (Sigma-Aldrich), and peritoneal macrophages were collected 4 days later. Phagocytosis was assayed by following the transport of pHrodo-stained prey into macrophage lysosomes (50, 51). In brief, $5 \times 10^5$ thio-pMacs were grown overnight in 12-well plates (Corning). Growing or apoptotic cells ($2.0 \times 10^7$) were washed with PBS and incubated with 40 ng/ml pHrodo for 10 min at room temperature. After stopping the reaction with 2 ml FCS, the cells were washed with IMDM containing 10% FCS, added to the macrophages in the medium containing 1% methyl cellulose (Sigma-Aldrich), spun at 500×g for 4 min at room temperature using a swinging rotor, and incubated at 37° C. The macrophages were detached from the plate by treatment with 0.25% trypsin, stained with APC-conjugated rat anti-mouse Mac1, suspended in 20 mM CHES-NaOH buffer (pH 9.0) containing 150 mM NaCl, 2% FCS, and 200 nM Sytox blue, and analyzed by flow cytometry using the FACSCanto II. Phagocytosis was defined as the percentage of pHrodo-positive cells in the Mac-1$^+$ Sytox blue$^-$ population.

For time-lapse observation, thio-pMacs ($5 \times 10^4$) were grown overnight in eight-well Lab-Tek II chambers coated with fibronectin. The pHrodo-labeled cells ($2 \times 10^5$) in IMDM containing 10% FCS, 1% methylcellulose and 5 µM CellEvent™ Caspase-3/7 Green were added to the macrophages, and the mixture was spun at 500×g for 4 min at room temperature. The cell culture was followed for 3-4 h in real time using a confocal microscope (FV1000-D), and images were captured every 1-2 min.

Electron Microscopy

Mouse thio-pMacs were incubated for 2 h with prey in IMDM containing 10 FCS and 1% methylcellulose as described above. Macrophages were then detached from the plate by scraping, and fixed by incubation at 4° C. overnight in PBS containing 4% paraformaldehyde and 2% glutaraldehyde (Nacalai Tesque). After washing with 0.1 M phosphate buffer 3 times, the samples were post-fixed at 4° C. for 2 h with 1% $OsO_4$ in 0.1 M phosphate buffer, and dehydrated by successive incubations in serially diluted ethanol (50, 60, 70, 80, 90, and 99% ethanol) for 20 min each, followed by dipping into 100% ethanol for 30 min twice. The samples were incubated sequentially in propylene oxide for 1 h, in a 1:1 mixture of propylene oxide and epoxide (Luveak 812, Nacalai Tesque) for 1.5 h, in a 1:3 mixture of propylene oxide and epoxide for 1.5 h, and in epoxide for 12 h, and the sequential incubation procedure was repeated. They were then embedded in epoxide by incubating at 60° C. for 3 days. Ultrathin sections (60-80 nm) were cut with an ultramicrotome EM UC6 (Leica), stained with uranyl acetate and lead citrate, and observed with an electron microscope H-7650 (Hitachi).

Internalization of NBD Lipids

Cells ($2 \times 10^6$) were incubated with 1.5 µM NBD-PS, NBD-PE, or NBD-PC at 25° C. for 15-20 min in 600 µl of HBSS containing 1 mM $MgCl_2$ and 2.5 mM $CaCl_2$. After incubation, the cells were collected by centrifugation, resuspended in HBSS containing 5 mg/ml fatty-acid-free BSA, and analyzed by a FACSAria II. To determine the scramblase activity, $1.5 \times 10^6$ cells were incubated at 25° C. for 4 min with 0.5 µM NBD-PC.

Tumor Development

To develop tumor in nude mice, $1 \times 10^6$ cells were subcutaneously injected into 7-week-old female BALB/c athymic nude mice. Four weeks later, the tumors were dissected and weighed.

Real-Time RT-PCR and PCR

RNA was prepared with Isogen (Nippon Gene) and the RNeasy Mini Kit (Qiagen), and was reverse-transcribed with a High Capacity RNA-to-cDNA™ Kit (Life Technologies, Applied Biosystems). The cDNA was amplified using LightCycler 480 SYBR Green I Master (Roche Diagnostics). Primers for real-time RT-PCR were: hCDC50A, 5'-CGATGGCGATGAACTATAACGC-3' (SEQ ID NO: 29) and 5'-CGGTATAATCAATCTCGATCTC-3' (SEQ ID NO: 30); hATP11C, 5'-GGAACGTAATGCAATGGATGGG-3' (SEQ ID NO: 31) and 5'-GGT-TAGTTCTAAGAGCTCAGTG-3' (SEQ ID NO: 32); hβ-actin, 5'-GCATCCTCACCCTGAAGTAC-3' (SEQ ID NO: 33) and 5'-CTTAATGTCACGCACGATTTC-3' (SEQ ID NO: 34); mCDC50A, 5'-TGCCAACAGCATGTT-TAATGA-3' (SEQ ID NO: 35) and 5'-TTCGAGGCTCTCTTTTCCAG-3' (SEQ ID NO: 36); mCDC50B, 5'-AACGACTCCTTCTCGCTCTG-3' (SEQ ID NO: 37) and 5'-CACGAAGTCCTGGTTGATGA-3' (SEQ ID NO: 38); mCDC50C, 5'-TTTCGGAATCCAA-GATCCAG-3' (SEQ ID NO: 39) and 5'-CAGTCGGCGGTACAGTTTTT-3' (SEQ ID NO: 40); mATP11C, 5'-TTACAGTTGGGGCCCTTCTT-3' (SEQ ID NO: 41) and 5'-TATCCAAGGCGAGCTTCAGA-3' (SEQ ID NO: 42); and mβ-actin, 5'-TGTGATGGTGG-GAATGGGTCAG-3' (SEQ ID NO: 43) and 5'-TTTGATGT-CACGCACGATTTCC-3' (SEQ ID NO: 44). The PCR analysis for P4-ATPase and CDC50 family members in KBM7 cells was carried out with specific primers described by Takatsu et al (52).

Statistical Analysis

All data were expressed as the mean with S.D. The statistical significance of the differences between groups was determined using Student's t-test.

2. Results

Haploid Genetic Screen for Phospholipid Flippases

Figure 1B:
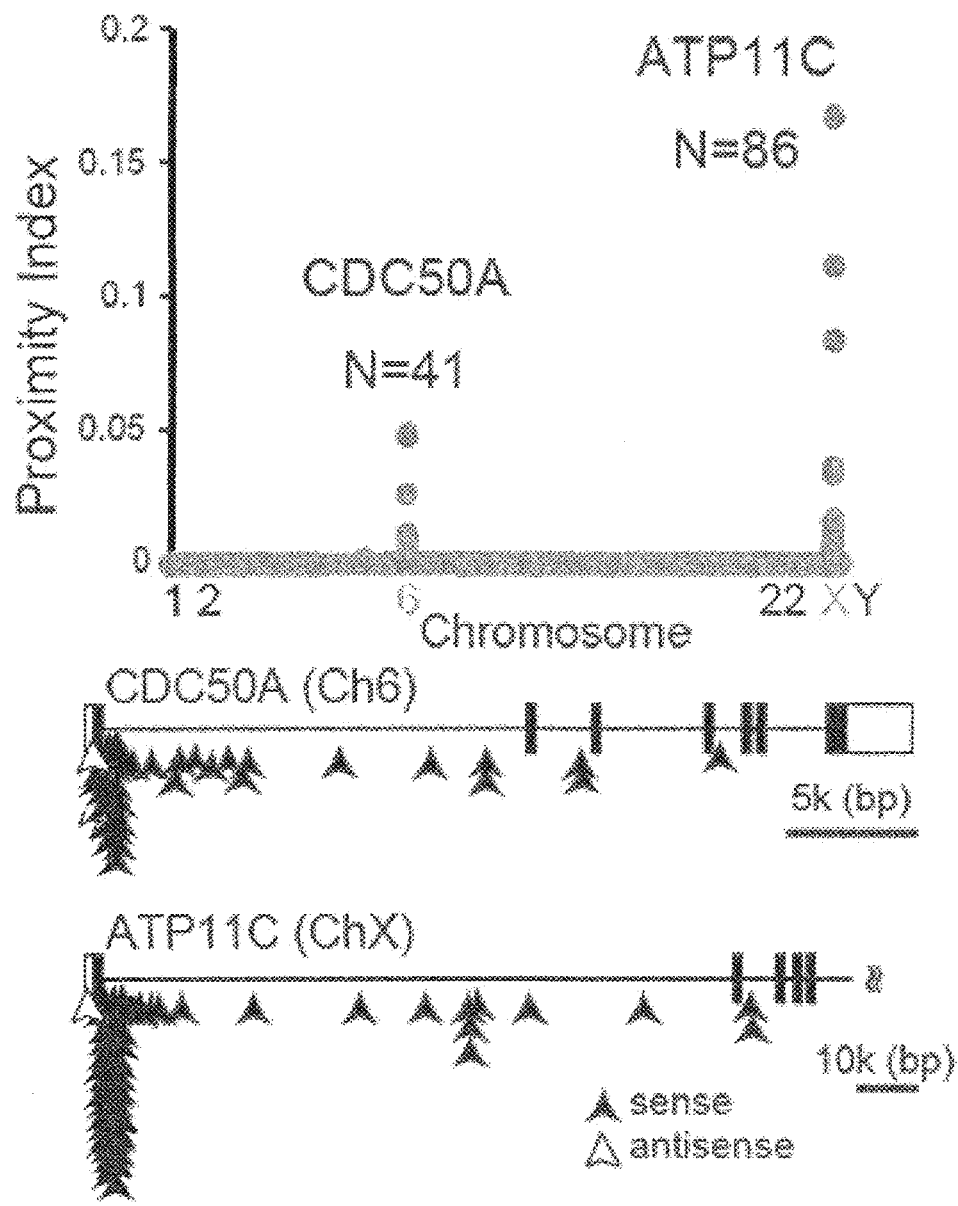
FIG. 1B Genetic screening using haploid cells (B). Sites of gene-trap insertion of retrovirus were identified by mass sequencing, and the proximity index was plotted for each human chromosome. The mutated genes (CDC50A and ATP11C) are indicated with the number (N) of retrovirus insertions. In the intron-exon structures of the entire CDC50A and exons 1-5 of ATP11C, arrows indicate the insertion positions (black, sense orientation; white, antisense orientation).

To identify flippase-encoding genes, we used a haploid genetic screen in human leukemia KBM7, which has a haploid karyotype except for chromosome 8 (16). KBM7 incorporated NBD-PS, indicating that they express flippase(s). KBM7 was mutagenized by infection with a retroviral gene trap vector, incubated with NBD-PS, and subjected to flow cytometry. Approximately 1.0% of the cells that exhibited defective NBD-PS internalization was collected, expanded, and subjected to second sorting (FIG. 1A), giving rise to cells having reduced flippase activity (LF, Low Flipping cells). Gene-trap insertion sites were recovered by inverse PCR with DNA from LF, and identified by massive sequencing (17). Analysis of the proximity index, for genomic regions containing multiple gene trap insertions in close proximity, identified two genes (FIG. 1B). Forty-one insertions were in CDC50A (Cell cycle control protein 50A or TMEM30A), and 86 insertions in ATP11C. Based on the information from human genome database (UCSC Genome Browser, http://genome.ucsc.edu/cgibin/hgTracks?org=human) and 5'-RACE analysis (FIG. 7), most of the insertions were assigned to intron 1 in the same transcriptional direction (FIG. 1B). Insertions in the reverse orientation were in exon 1 or the promoter region, suggesting that these insertions also inactivated the gene function.

Figure 1C:
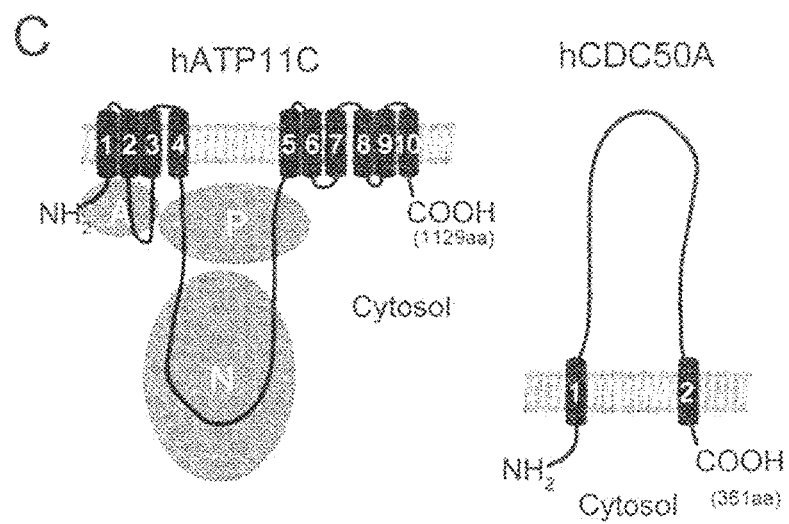
FIG. 1C Genetic screening using haploid cells (C). The structures of hATP11C and hCDC50A are shown, with transmembrane segments numbered. In hATP11C, three cytoplasmic domains (A: actuator, P: phosphorylation, and N: Nucleotide binding) predicted by similarity to SERCA2a (40) are show in circles.
Figure 1D:
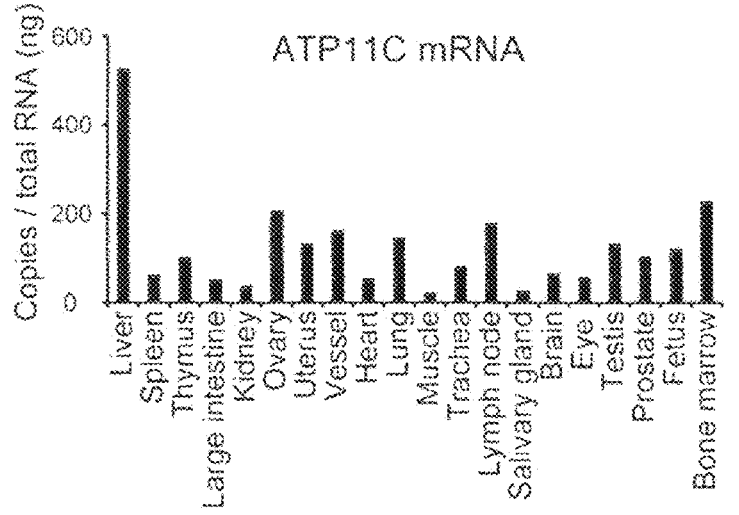
FIG. 1D Genetic screening using haploid cells (D). ATP11C and CDC50A mRNA levels in the indicated mouse tissues were determined by real-time RT-PCR, and expressed as copy numbers relative to 1.0 ng total RNA.
Figure 1D:
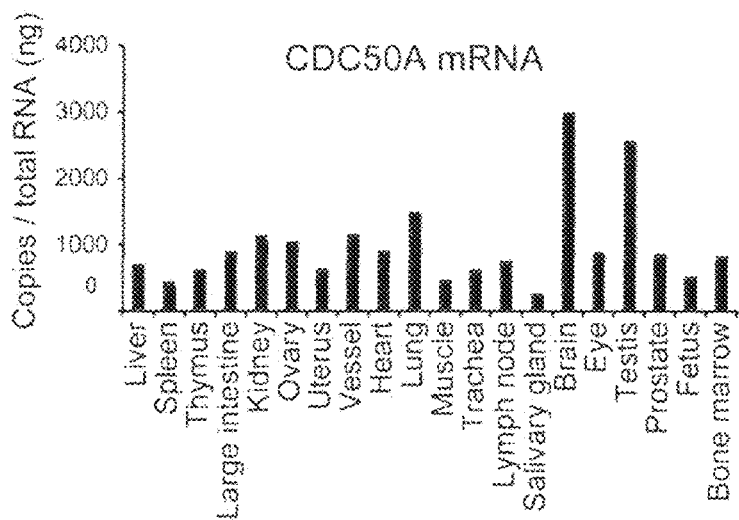
Figure 1E:
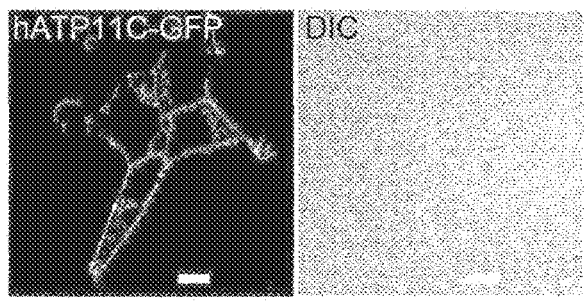
FIG. 1E Genetic screening using haploid cells (E). Human HEK293T expressing hATP11C-GFP was examined by fluorescence confocal microscopy. DIC, differential interference contrast. Scale bar, 10 μm.
Figure 2A:
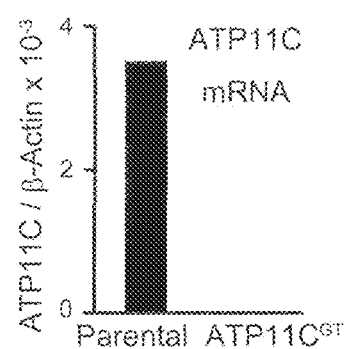
FIG. 2A Requirement of ATP11C and CDC50A for flippase activity (A). ATP11C and CDC50A mRNA levels were determined by real-time RT-PCR, and expressed relative to β-actin mRNA in KBM7, ATP11C$^{GT}$, and CDC50A$^{GT}$.
Figure 2A:
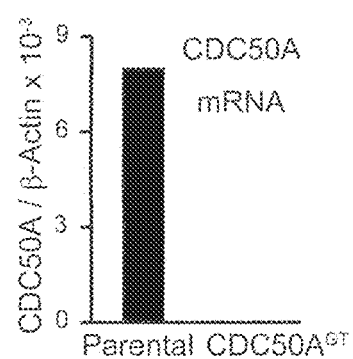
Figure 2B:
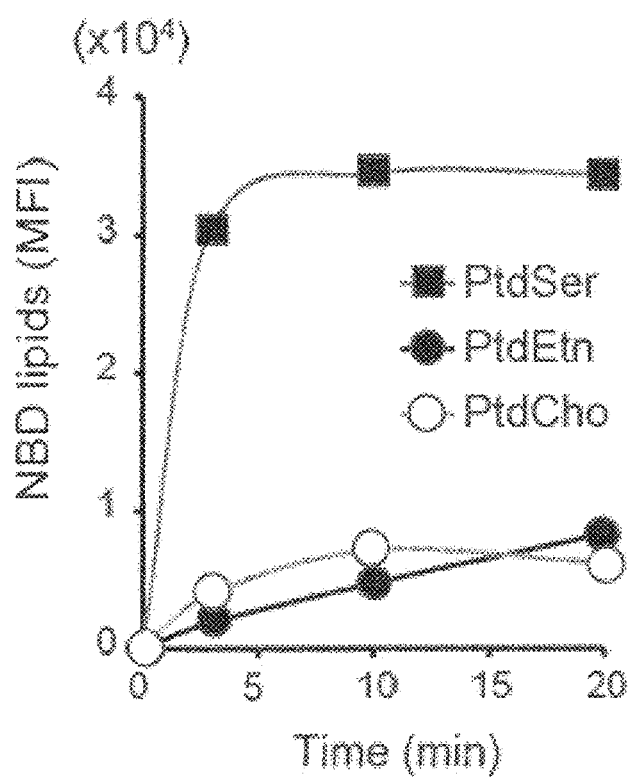
FIG. 2B Requirement of ATP11C and CDC50A for flippase activity (B). KBM7 was incubated with 1.5 μM NBD-PS (PtdSer), NBD-PE (PtdEtn), or NBD-PC (PtdCho), treated with fatty-acid-free BSA, and analyzed by flow cytometry. The mean fluorescent intensity (MFI) was plotted.
Figure 2C:
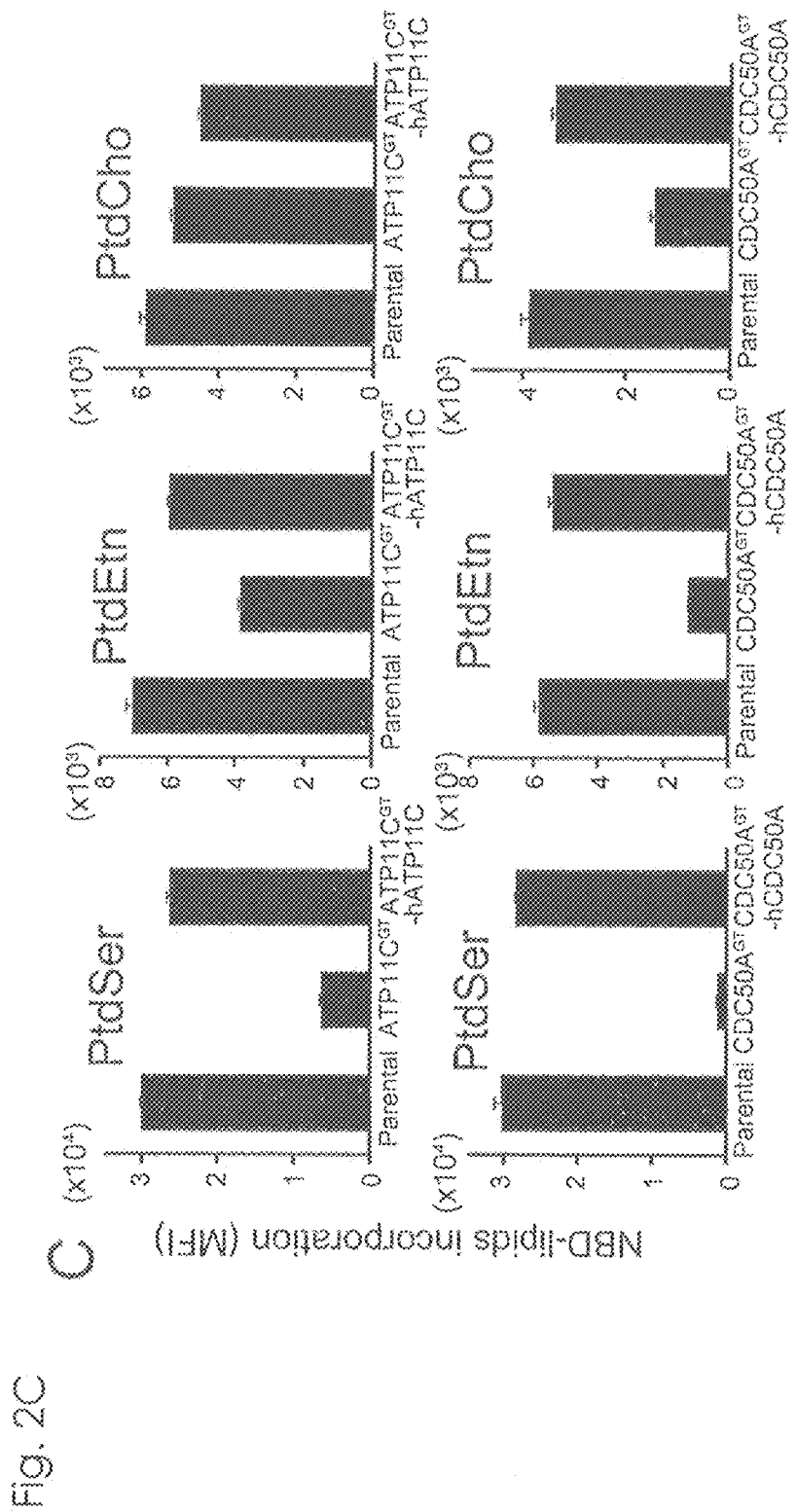
FIG. 2C Requirement of ATP11C and CDC50A for flippase activity (C). KBM7, ATP11C$^{GT}$, CDC50A$^{GT}$, and their transformants expressing hATP11C or hCDC50A, were incubated for 20 min with the indicated NBD-phospholipids, and analyzed by flow cytometry. MFI was plotted (n=3).
Figure 2D:
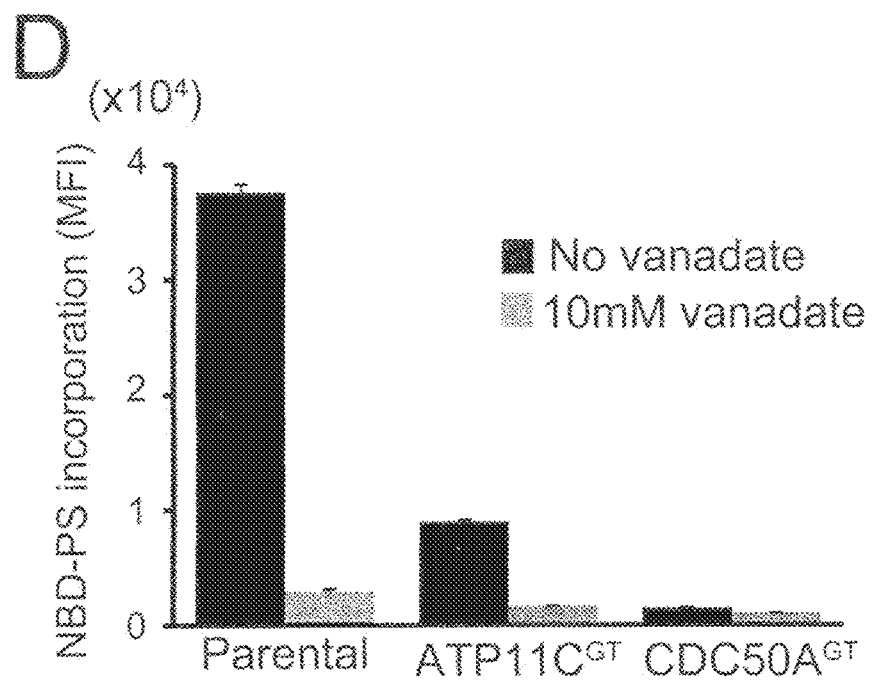
FIG. 2D Requirement of ATP11C and CDC50A for flippase activity (D). KBM7, ATP11C$^{GT}$, and CDC50A$^{GT}$ were incubated for 20 min with NBD-PS with or without an ATPase inhibitor vanadate, and analyzed by flow cytometry. MFI was plotted (n=3).
Figure 2E:
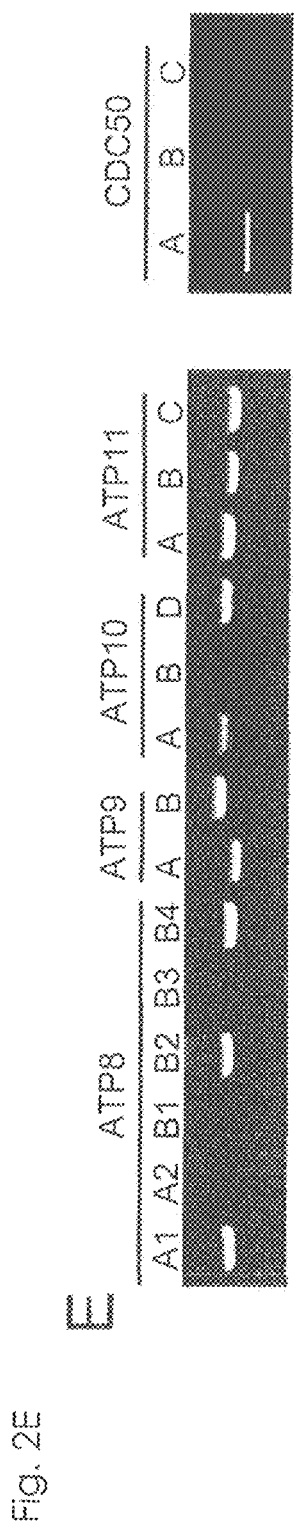
FIG. 2E Requirement of ATP11C and CDC50A for flippase activity (E). mRNA from KBM7 was analyzed by RT-PCR for the indicated P4-ATPase or CDC50 family members.
Figure 2F:
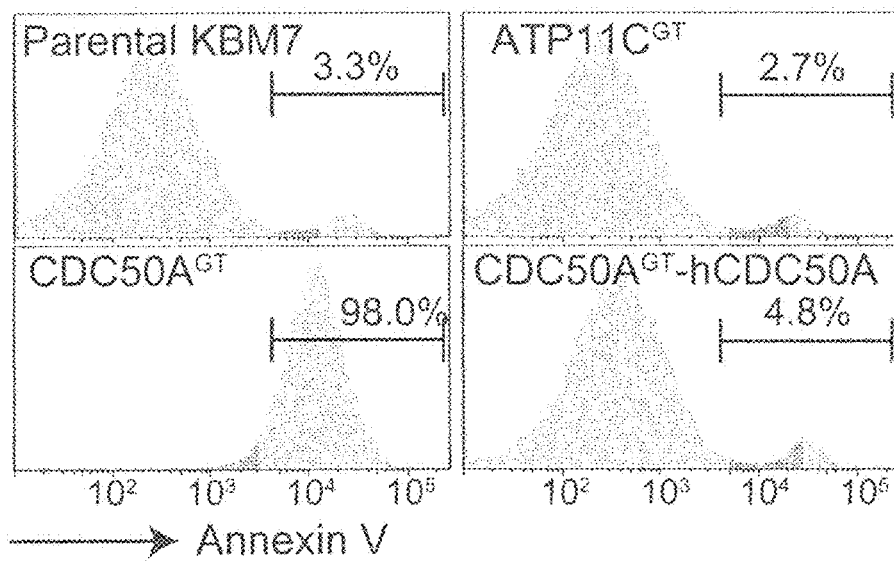
FIG. 2F Requirement of ATP11C and CDC50A for flippase activity (F). KBM7, ATP11C$^{GT}$, CDC50A$^{GT}$, and CDC50A$^{GT}$ transformant expressing hCDC50A were stained with Cy5-Annexin V and Sytox Blue. Annexin V-staining profile of the Sytox Blue-negative population is shown with the percentage of Annexin V-positive cells.

ATP11C with 10 transmembrane regions (FIG. 1C) is a member of P4-ATPase family, and CDC50A with 2 transmembrane regions is a β-subunit of P4-ATPases (12, 18). They were expressed in various tissues (FIG. 1D). ATP11C-GFP expressed in human HEK293T was localized primarily to the plasma membrane (FIG. 1E). Cells (ATP11C$^{GT}$ and CDC50A$^{GT}$) carrying insertions in the first intron of ATP11C or CDC50A gene were isolated by limiting dilution (FIG. 2A). KBM7 incorporated high levels of NBD-PS (FIG. 2B), which was significantly reduced in ATP11C$^{GT}$. The incorporation of NBD-PE, but not NBD-PC, was also reduced in ATP11C$^{GT}$, and the transformation with human (h)ATP11C fully rescued the flippase activity (FIG. 2C). The incorporation of phospholipids in ATP11C$^{GT}$ was inhibited by an ATPase inhibitor, orthovanadate (FIG. 2D), suggesting that the remaining flippase activity in these cells was due to other ATPases expressed in KBM7 (FIG. 2E). Among the three members of CDC50 family, only CDC50A was expressed in KBM7 (FIG. 2E), and the internalization of NBD-PS and NBD-PE was completely defective in CDC50A$^{GT}$, which was rescued by transformation with hCDC50A (FIG. 2C). The lack of PtdSer-flippase in CDC50A$^{GT}$ resulted in constitutive PdtSer exposure on cell-surface (FIG. 2F). This contrasted with the ATP11C$^{GT}$, which did not expose PtdSer, and suggested that the residual PtdSer-flippase in ATP11C$^{CT}$ was sufficient to maintain the asymmetrical PtdSer distribution. The ability to internalize NBD-PC was also reduced in CDC50A$^{GT}$ (FIG. 2C), suggesting that some P4-ATPases expressed in KBM7 may promote PtdCho flipping.

Caspase-Mediated ATP11C Cleavage During Apoptosis

Figure 3A:
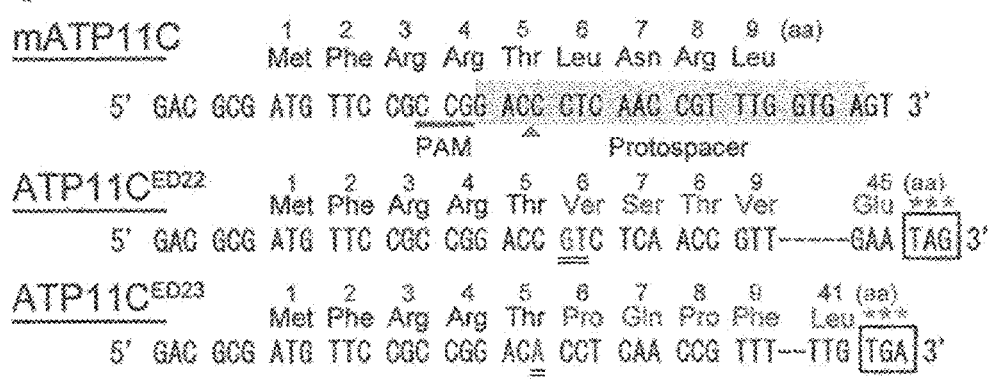
FIG. 3A Cleavage of ATP11C by caspase (A). mATP11C in W3 was mutated using CRISPR-Cas. Protospacer sequence is highlighted, protospacer-adjacent motif (PAM) is underlined, and the cleavage site is indicated by arrowhead. ATP11C in ATP11C$^{ED22}$ and ATP11C$^{ED23}$ carries a biallelic insertion of "GT" or "A" (doubly underlined), causing loss of gene function.
Figure 8A:
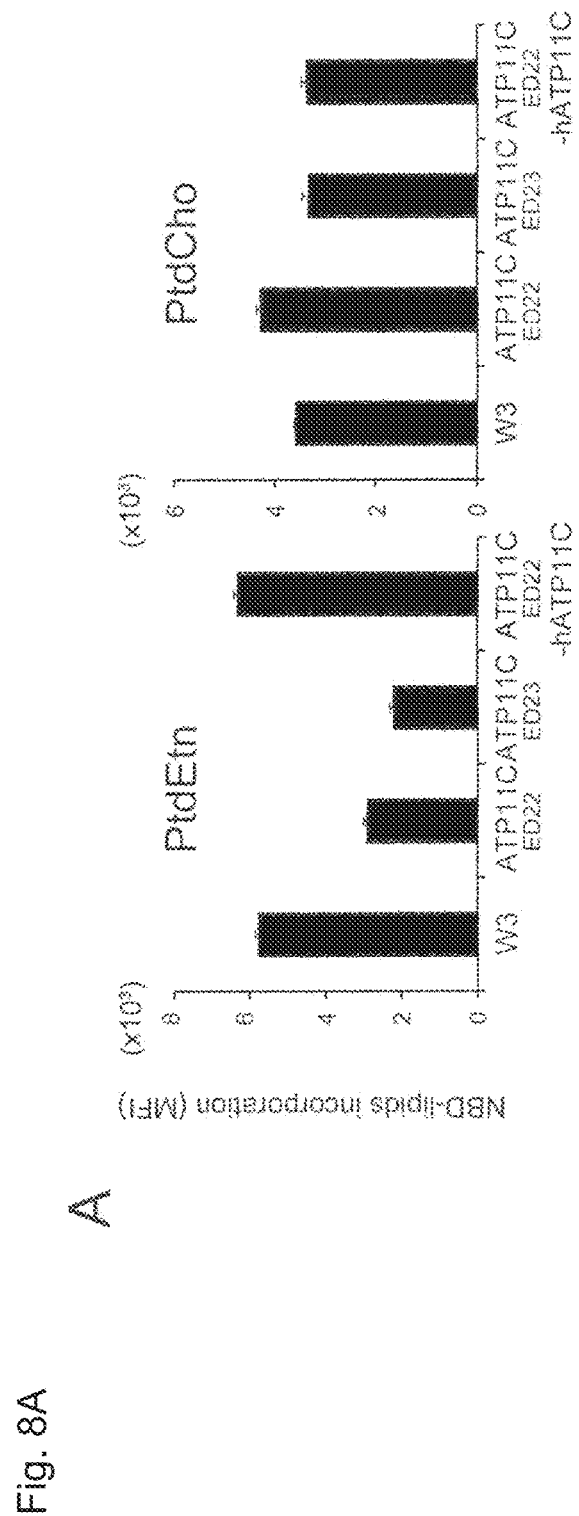
FIG. 8A Effect of ATP11C deficiency on phospholipid incorporation (A). W3, ATP11C$^{ED}$ mutants (ATP11C$^{ED22}$ and ATP11C$^{ED23}$), and ATP11C$^{ED22}$ expressing hATP11C were incubated for 15 min at room temperature with 1.5 µM NBD-PE (PtdEtn) or NBD-PC (PtdCho). The cells were treated with fatty-acid-free BSA, and analyzed by flow cytometry. Incorporated NBD-lipid was quantified, and expressed as MFI (mean+SD) (n=3).

Mouse (m) ATP11C was then mutated using the CRISPR/Cas (clustered regulatory interspaced short palindromic repeats/cas) system (19) in W3. This procedure generated 4 clones carrying insertions resulting in ATP11C truncations and inactivation, two of which (ATP11C$^{ED22}$ and ATP11C$^{ED23}$) were further characterized (FIG. 3A). The internalization of NBD-PS and NBD-PE, but not NBD-PC was strongly reduced in ATP11C$^{ED22}$ and ATP11C$^{ED23}$ (FIGS. 3B and 8A).

Figure 3C:
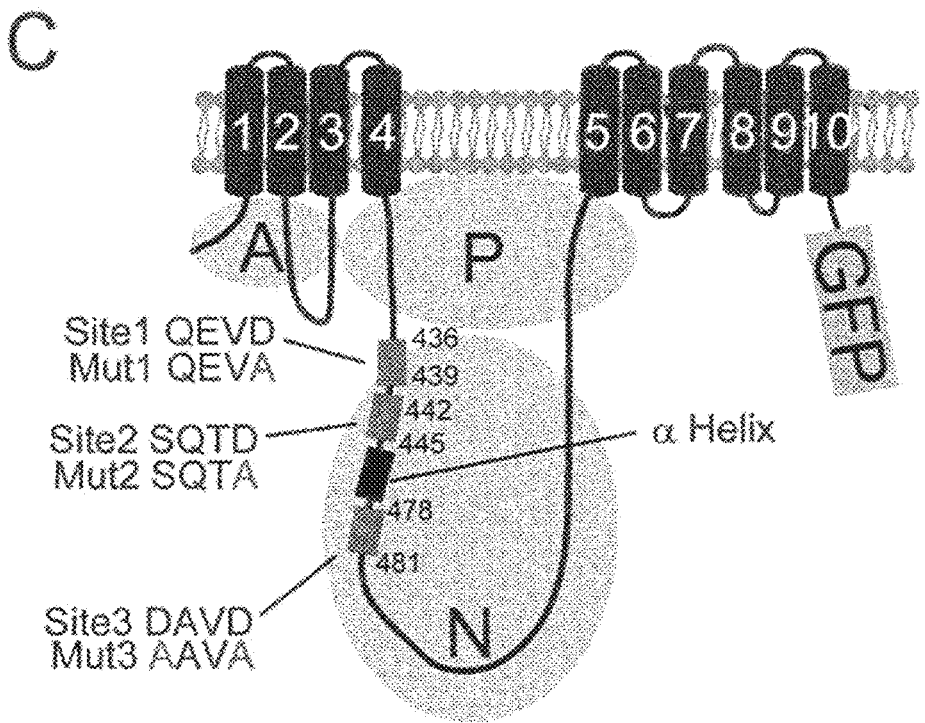
FIG. 3C Cleavage of ATP11C by caspase (C). The structure of hATP11C-GFP with caspase-recognition sites and α-helix is shown. Amino acid sequences around the caspase-recognition sites in 6 vertebrate ATP11C are aligned with * for residues conserved in all members.
Figure 3D:
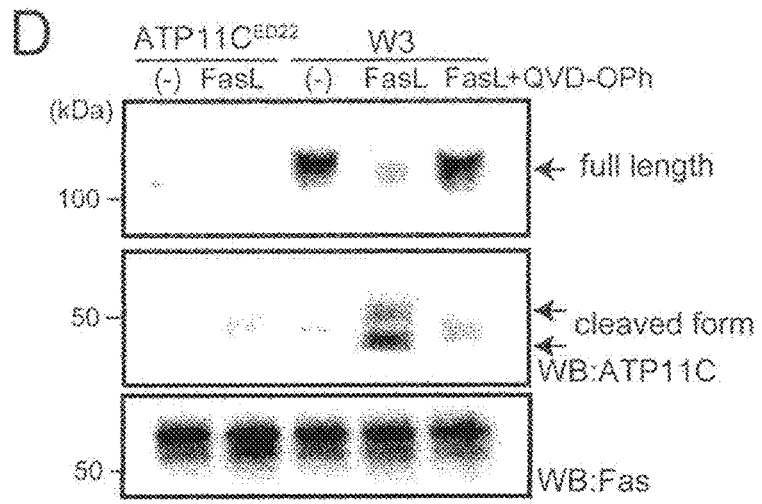
FIG. 3D Cleavage of ATP11C by caspase (D). W3 and ATP11C$^{ED22}$ were incubated for 1 h with FasL in the presence or absence of 20 μM QVD-Oph. Membrane fractions were analyzed by Western blotting with anti-mATP11C or anti-mFas. Upper and middle panels: the blot with anti-mATP11C, where exposure time is longer in the middle panel.
Figure 3E:
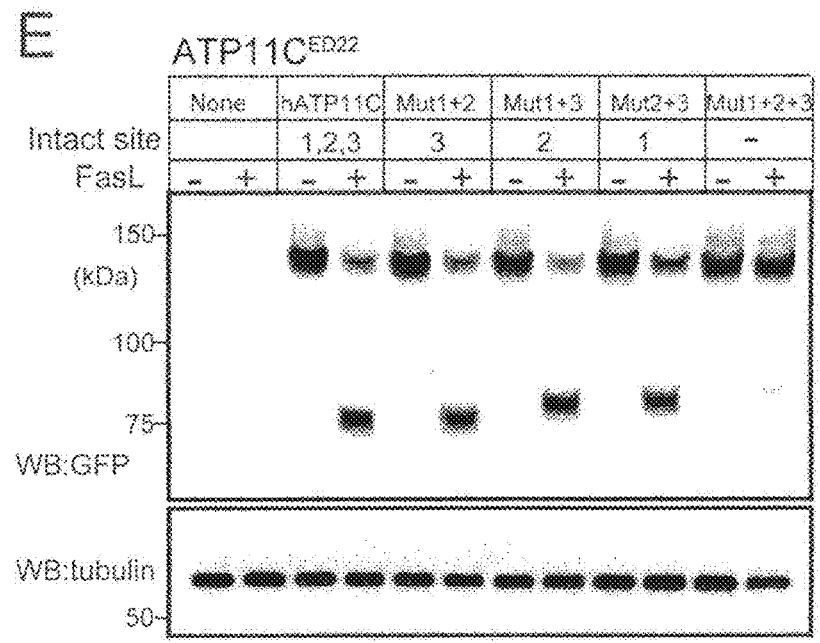
FIG. 3E Cleavage of ATP11C by caspase (E). ATP11C$^{ED22}$ and its transformants expressing the wild-type or mutant hATP11C-GFP were incubated for 45 min with FasL, and analyzed by Western blotting with anti-GFP.
Figure 3F:
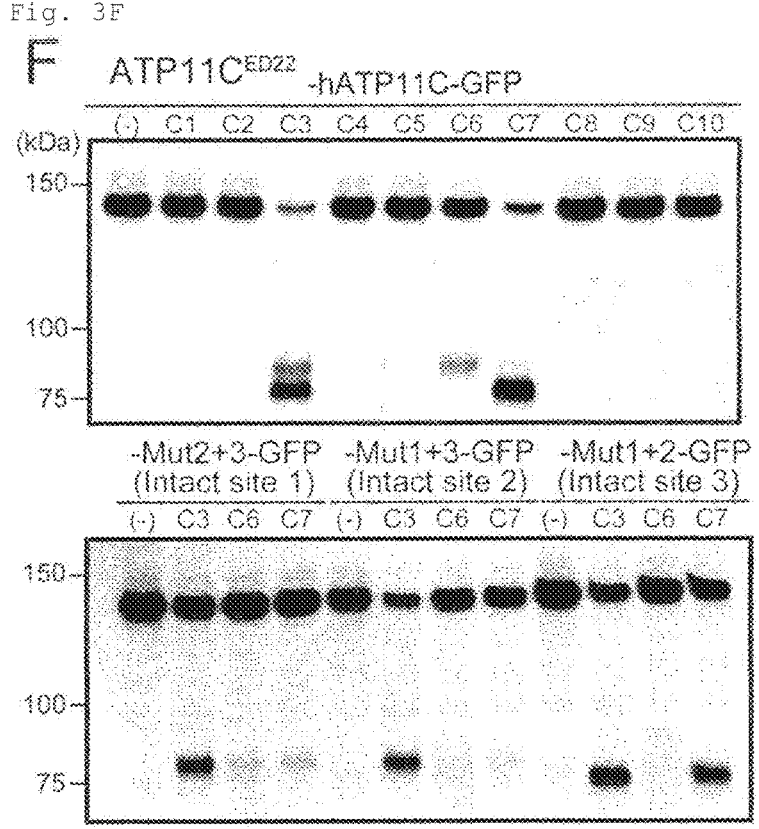
FIG. 3F Cleavage of ATP11C by caspase (F). Solubilized membrane fractions of ATP11C$^{ED22}$ transformants expressing wild-type or mutant ATP11C-GFP were incubated with different caspases (C1 to C10, caspase-1-10) or untreated (−), and analyzed by Western blotting with anti-GFP.
Figure 8B:
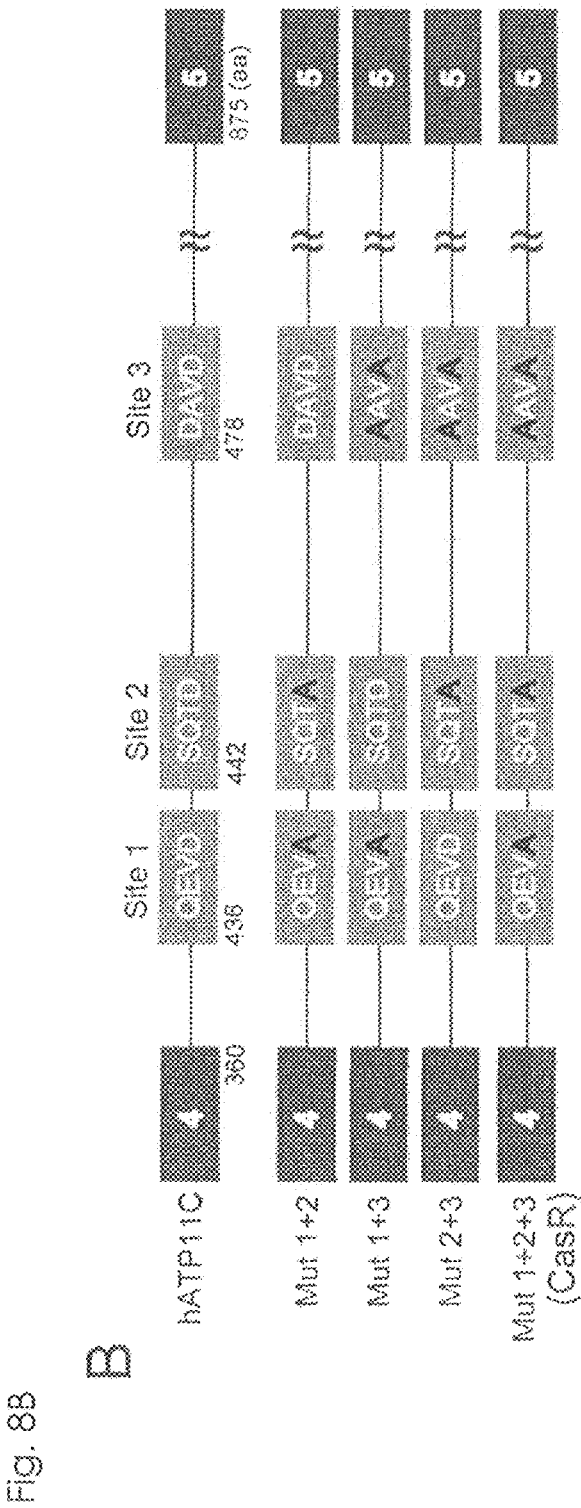
FIG. 8B Effect of ATP11C deficiency on phospholipid incorporation (B). Schematic representation of human ATP11C caspase-recognition site mutants. The three caspase-recognition sites located in the second cytoplasmic loop between transmembrane segments 4 and 5 of hATP11C are schematically shown. In the indicated mutants, the aspartic acid residues in the caspase-recognition sites (Sites 1-3) were mutated to alanine residues. In the Mut 1+2, 1+3, and 2+3 mutants, 2 caspase-recognition sites were mutated in different combinations, while all 3 recognition sites were mutated in the Mut 1+2+3 mutant (CasR).

The apoptotic PtdSer exposure is accompanied by the loss of flippase activity (14, 15). Treating W3 with hFas ligand (FasL) caused a shift in ATP11C's mobility (from 120 to 50 kDa) as shown in electrophoresis using SDS (FIG. 3D), which could be prevented by a caspase inhibitor (Q-VD-OPh). A search for caspase-recognition sequences in hATP11C using Cascleave (http://sunflower.kuicr.kyoto-u.ac.jp/~sjn/Cascleave/) revealed three sites (Sites 1-3) in the Nucleotide-binding or "N" domain (QEVDG (SEQ ID NO: 45), SQTDG (SEQ ID NO: 46), and DAVDG (SEQ ID NO: 47), respectively) (FIG. 3C). These sites flanking an α-helix were evolutionarily conserved. The sequences in Sites 1-3 were changed to QEVAG (Mut1) (SEQ ID NO: 48), SQTAG (Mut2) (SEQ ID NO: 49), and AAVAG (Mut3) (SEQ ID NO: 50). Double or triple mutants (FIG. 8B) were generated, tagged by GFP at C-terminus, and expressed in ATP11C$^{ED22}$. The ATP11C$^{ED22}$ transformants were treated with FasL, and analyzed by Western blotting with anti-GFP (FIG. 3E). The FasL-treatment caused a shift of 140 kDa of the wild-type and doubly mutated hATP11C-GFP chimera (Mut1+2, Mut1+3, and Mut2+3) to about 80 kDa. While, little cleavage was observed with the triply mutated hATP11C-GFP (Mut1+2+3). Incubation of the solubilized membrane fraction from cells expressing hATP11C-GFP with caspases revealed that hATP11C was cleaved by caspase-3, -6 and -7 (FIG. 3F). In particular, caspase-3 cleaved hATP11C at all three positions. Since the amino acid sequence of mATP11C, including the caspase-recognition sites, is highly homologous (94.8% identity) to hATP11C, it is likely that mATP11C is also cleaved by caspase 3 during apoptosis.

Requirement of Caspase-Mediated ATP11C Cleavage for PtdSer Exposure

Figure 4A:
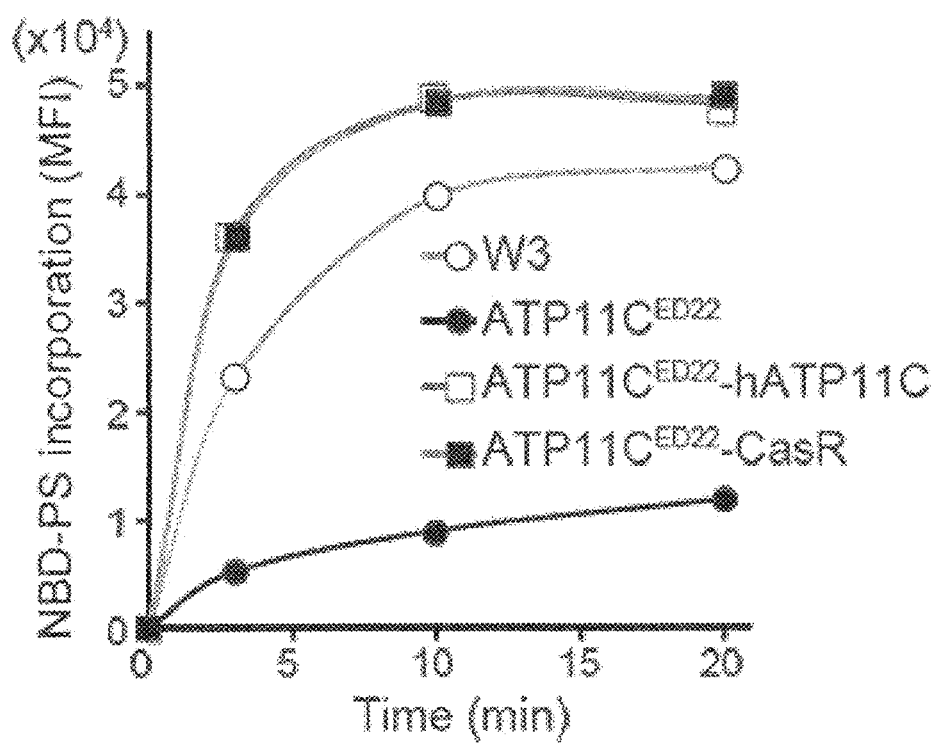
FIG. 4A Requirement of caspase-mediated ATP11C cleavage for apoptotic PtdSer-exposure (A). W3, ATP11C$^{ED22}$, and ATP11C$^{ED22}$ transformants expressing wild-type or caspase-resistant hATP11C (ATP11C$^{ED22}$-hATP11C or ATP11C$^{ED22}$-CasR) were incubated at 25° C. with NBD-PS, treated with BSA, and analyzed by FACS. The experiment was performed in triplicate, and mean MFI was plotted (n=3).
Figure 4B:
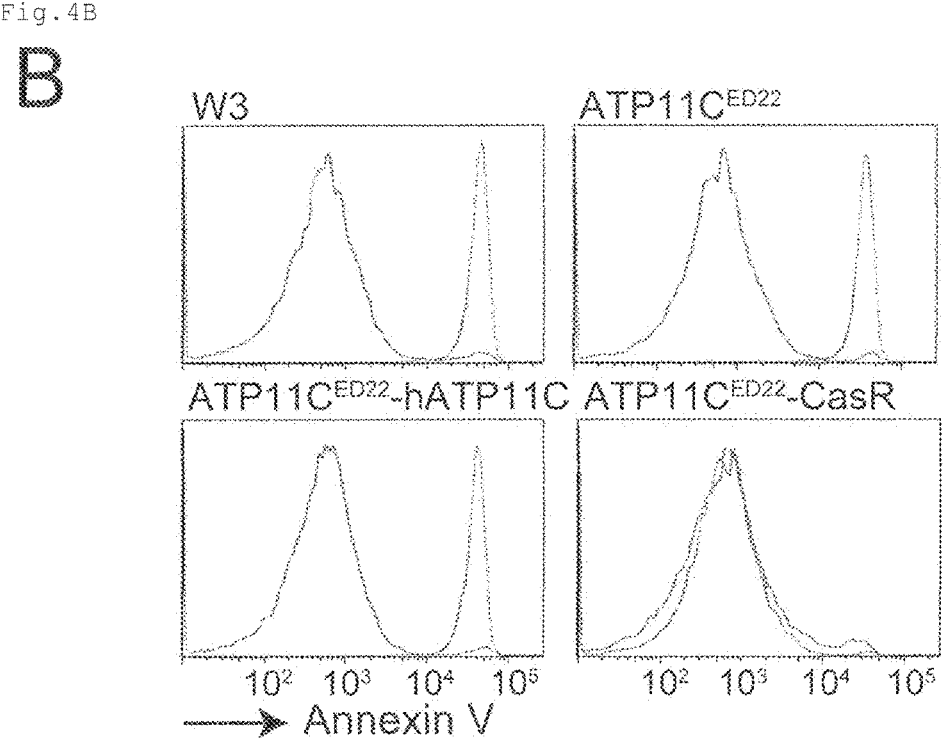
FIG. 4B Requirement of caspase-mediated ATP11C cleavage for apoptotic PtdSer-exposure (B). W3, ATP11C$^{ED22}$, ATP11C$^{ED22}$-hATP11C, and ATP11C$^{ED22}$-CasR were untreated or treated with FasL for 2 h. Annexin V-profile of Sytox blue-negative population is shown.
Figure 4C:
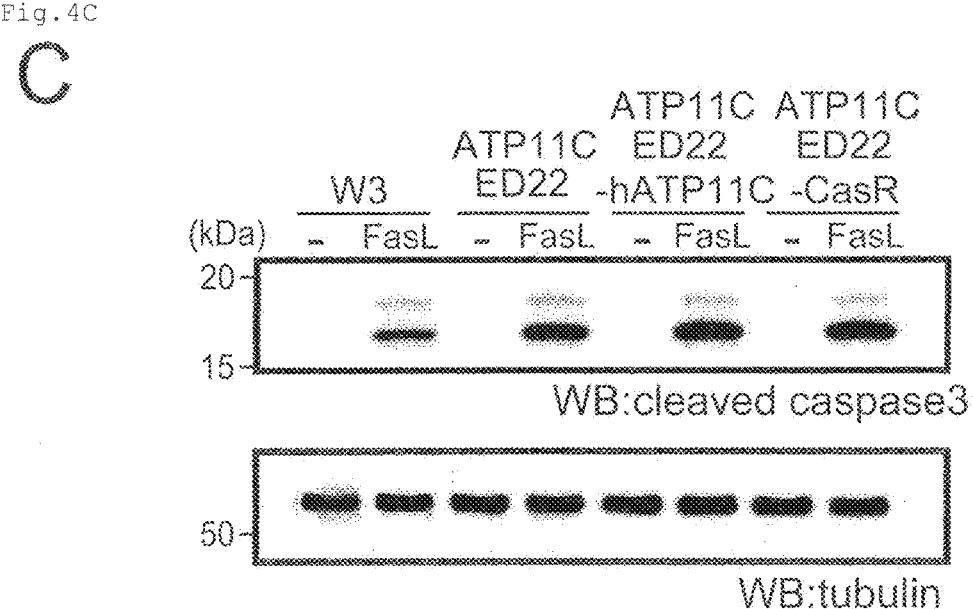
FIG. 4C Requirement of caspase-mediated ATP11C cleavage for apoptotic PtdSer-exposure (C). W3, ATP11C$^{ED22}$, ATP11C$^{ED22}$-hATP11C, and ATP11C$^{ED22}$-CasR were treated with FasL for 1 h. Cell lysates before or after the treatment were analyzed by Western blotting with anti-cleaved caspase-3 or anti-α-tubulin.
Figure 4D:
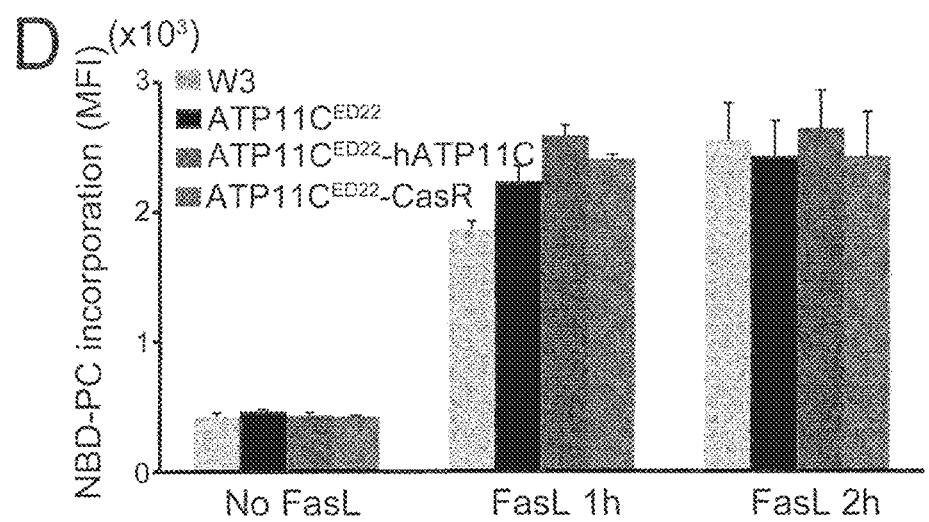
FIG. 4D Requirement of caspase-mediated ATP11C cleavage for apoptotic PtdSer-exposure (D). W3, ATP11C$^{ED22}$, and ATP11C$^{ED22}$ transformants expressing wild type hATP11C or CasR were untreated or treated for 1 or 2 h with FasL. Cells were then incubated at 25° C. with 0.5 μM NBD-PC for 4 min, and analyzed by FACS. The mean MFI was plotted (n=3). Each column in the series of column shows, from left to right, the data from W3, ATP11C$^{ED22}$, ATP11C$^{ED22}$-hATP11C, and ATP11C$^{ED22}$-CasR.

ATP11C$^{ED22}$ transformants expressing the caspase-resistant ATP11C (CasR) in which all three 3 caspase-recognition sites were mutated, incorporated NBD-PS as efficiently as those expressing wild-type ATP11C (FIG. 4A), indicating that CasR retained the flippase activity. This inhibited the apoptotic PtdSer exposure. FasL induced PtdSer-exposure in W3, ATP11C$^{ED22}$, and ATP11C$^{ED22}$ transformants expressing wild-type but not CasR (FIG. 4B), although caspase-3 was activated across the various cell types (FIG. 4C). CasR ATP11C had no effect on the FasL induced scrambling activity, measured by NBD-PC incorporation (FIG. 4D). These results indicated that the impaired FasL-induced PtdSer exposure in the CasR transformants was because ATP11C was not inactivated by caspases.

Figure 4E:
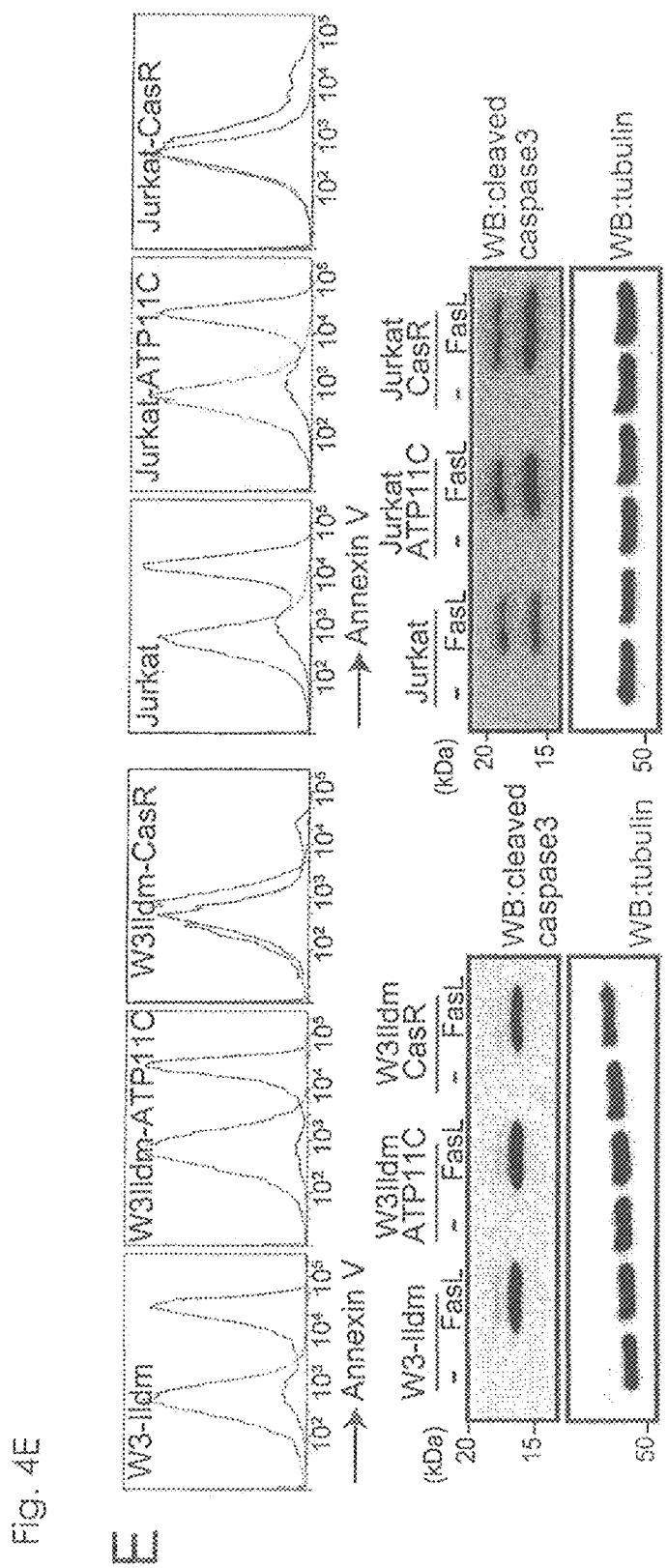
FIG. 4E Requirement of caspase-mediated ATP11C cleavage for apoptotic PtdSer-exposure (E). W3-Ildm and Jurkat were transformed with hATP11C or CasR to establish W3-hATP11C, W3-CasR, Jurkat-hATP11C, and Jurkat-CasR. These cells were treated with FasL, stained with Annexin V, and analyzed by FACS. As shown in the images in the bottom part, cell lysates were analyzed by Western blotting with anti-active caspase-3.
Figure 4F:
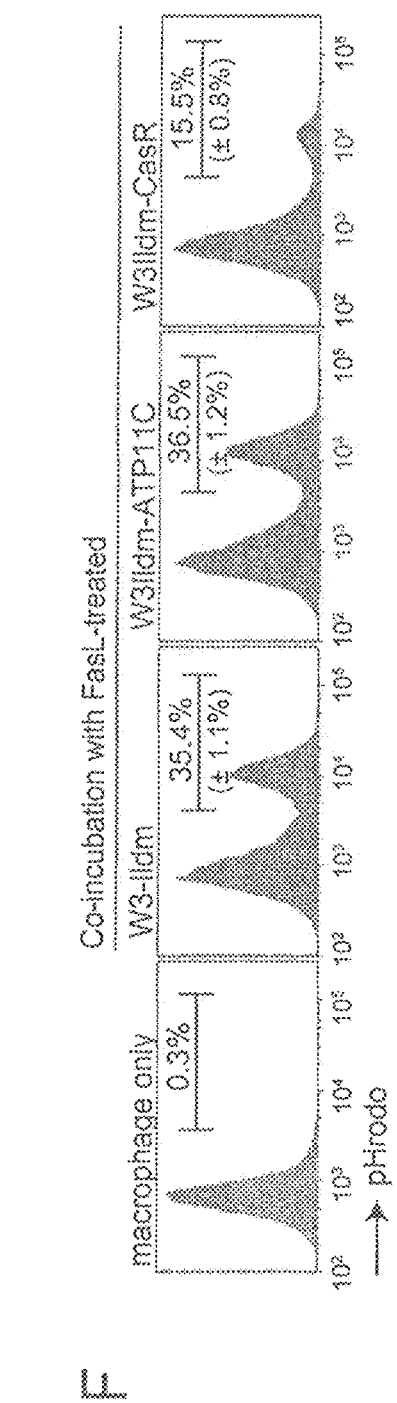
FIG. 4F Requirement of caspase-mediated ATP11C cleavage for apoptotic PtdSer-exposure (F). FasL-treated W3-Ildm, W3Ildm-hATP11C, and W3Ild-CasR were labeled with pHrodo, incubated for 1 h with thioglycollate-elicited peritoneal macrophage (thio-pMacs), and analyzed by flow cytometry.
Figure 9A:
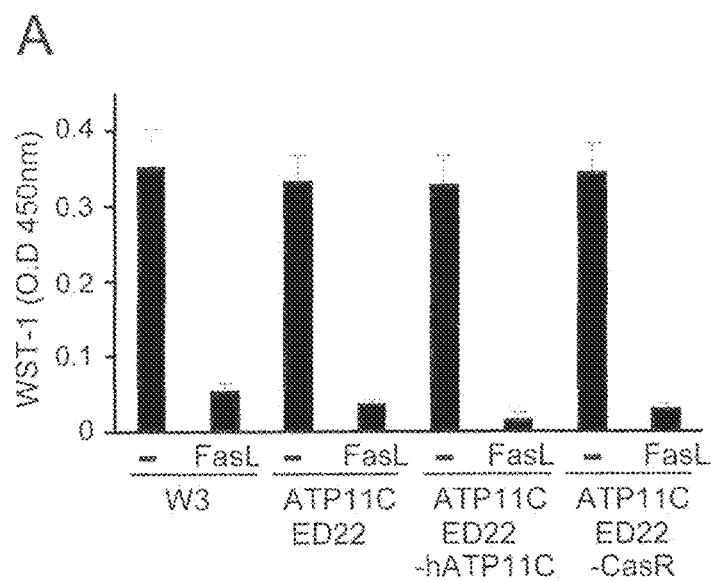
FIG. 9A No effect of the caspase-resistant hATP11C on FasL-induced cell death, DNA fragmentation, or cell shrinkage (A). W3, ATP11C$^{ED22}$, or ATP11C$^{ED22}$ transformants expressing hATP11C or its caspase-resistant form (CasR) were incubated with FasL for 2 h. FasL-induced cell death was analyzed with the WST-1 assay.
Figure 9B:
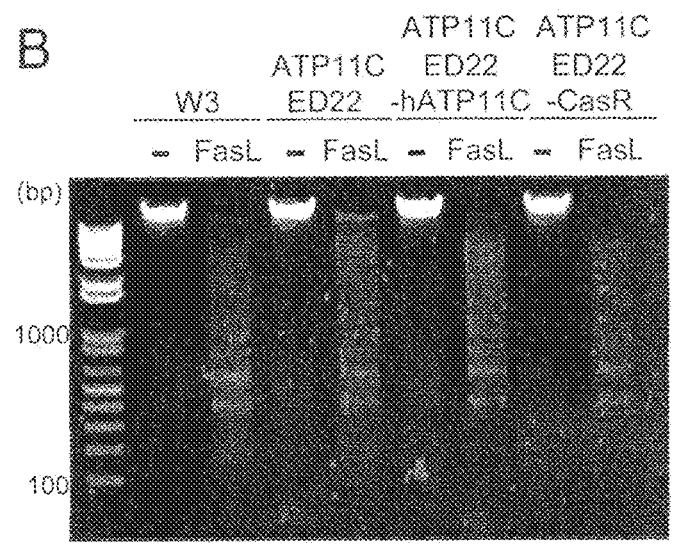
FIG. 9B No effect of the caspase-resistant hATP11C on FasL-induced cell death, DNA fragmentation, or cell shrinkage (B). Chromosomal DNA was prepared from untreated or FasL-treated cells, separated by electrophoresis on a 1.5% agarose gel, and stained with ethidium bromide.
Figure 9C:
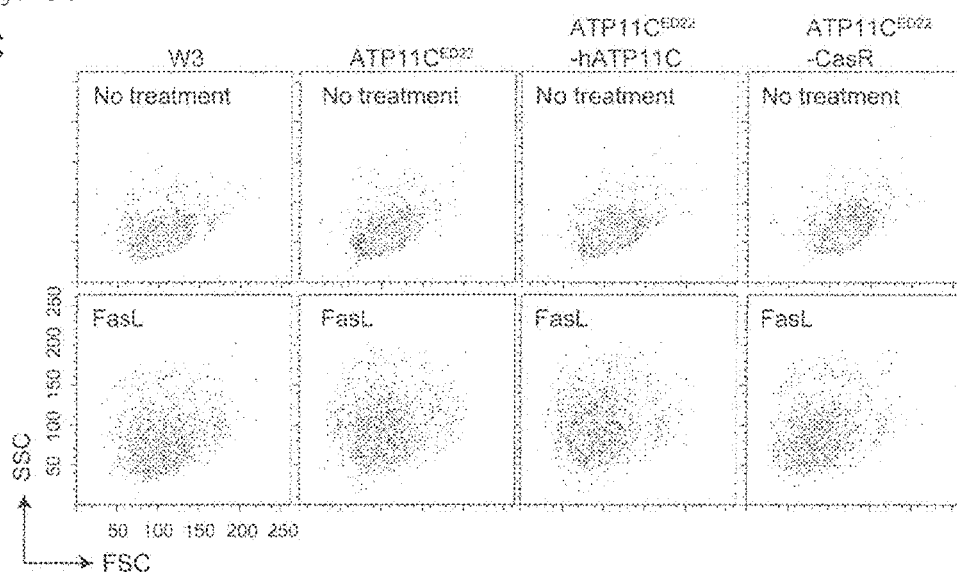
FIG. 9C No effect of the caspase-resistant hATP11C on FasL-induced cell death, DNA fragmentation, or cell shrinkage (C). Untreated or FasL-treated cells were analyzed by flow cytometry. The forward scatter (FSC) profile represents cell size.

In contrast to PtdSer exposure, FasL-induced cell death, cell shrinkage and DNA fragmentation were comparable in parental and CasR-expressing cells (FIGS. 9A to 9C). CasR blocked apoptotic PtdSer exposure in wild-type cells as well. W3-Ildm and Jurkat, and their hATP11C transformants (W3Ildm-hATP11C and Jurkat-hATP11C) exposed PtdSer by FasL-treatment (FIG. 4E). However, their transformants expressing CasR (W3Ildm-CasR and Jurkat-CasR) hardly exposed PtdSer upon FasL treatment. The FasL-treated parental and hATP11C-transformants were efficiently engulfed by thioglycollate-elicited peritoneal macrophages (thio-pMacs), while the CasR transformants were not (FIG. 4F), suggesting that flippase must be inactivated by caspase for the macrophage engulfment of apoptotic cells.

Constitutive PtdSer Exposure in Viable Cells that Lack CDC50A

Figure 5A:
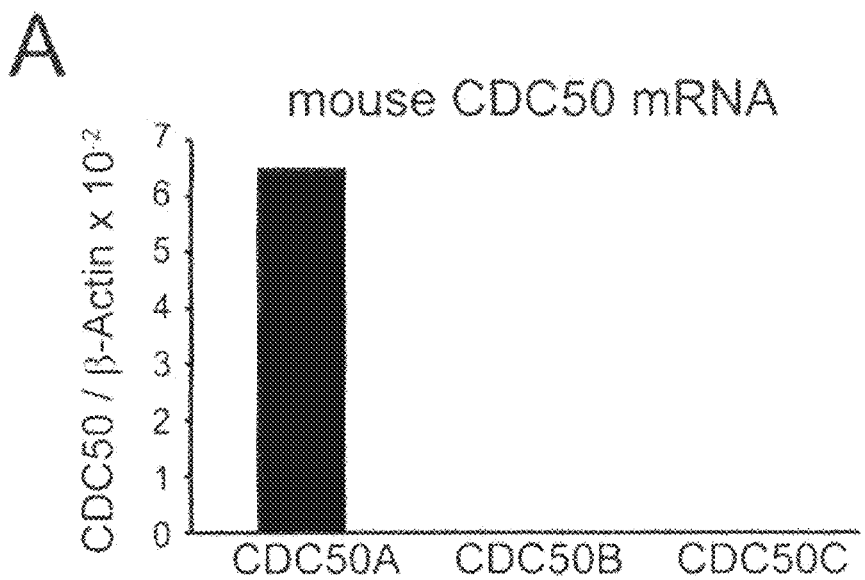
FIG. 5A Constitutive PtdSer exposure in viable CDC50A$^{-/-}$ cells (A). As shown in the figure, mRNA levels of mCDC50 members (50A, 50B and 50C) in W3-Ildm were determined by real-time PCR.
Figure 5B:
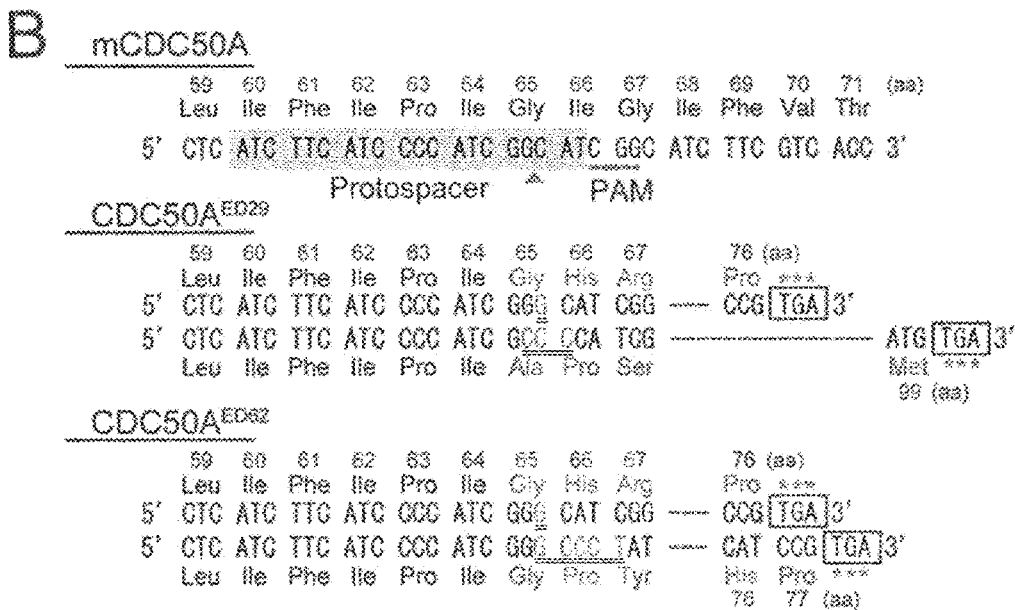
FIG. 5B Constitutive PtdSer exposure in viable CDC50A$^{-/-}$ cells (B). mCDC50A target sequence for Crisp-Cas. Protospacer sequence is shaded, protospacer-adjacent motif (PAM) is underlined, and the cleavage site is indicated by arrowhead. Two mutated cell clones (CDC50A$^{ED29}$ and CDC50A$^{ED62}$) carry different indels (doubly underlined) in two alleles, causing truncation of the protein at positions 76 and 99, and 76 and 77, respectively.
Figure 5C:
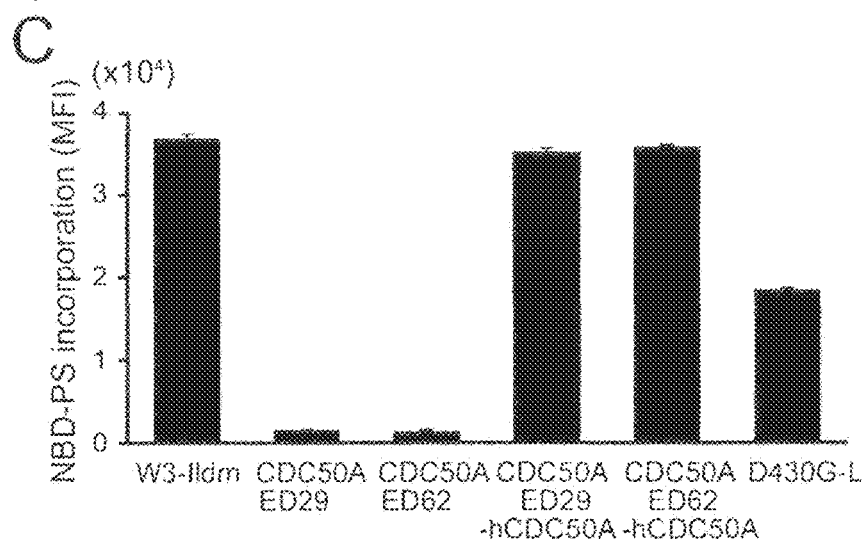
FIG. 5C Constitutive PtdSer exposure in viable CDC50A$^{-/-}$ cells (C). W3-Ildm, CDC50A$^{ED29}$ and CDC50A$^{ED62}$, their transformants expressing hCDC50A, and W3-D430G-L were incubated with NBD-PS for 15 min. Incorporated NBD-PS was quantified by FACS, and expressed as MFI (n=3).
Figure 5D:
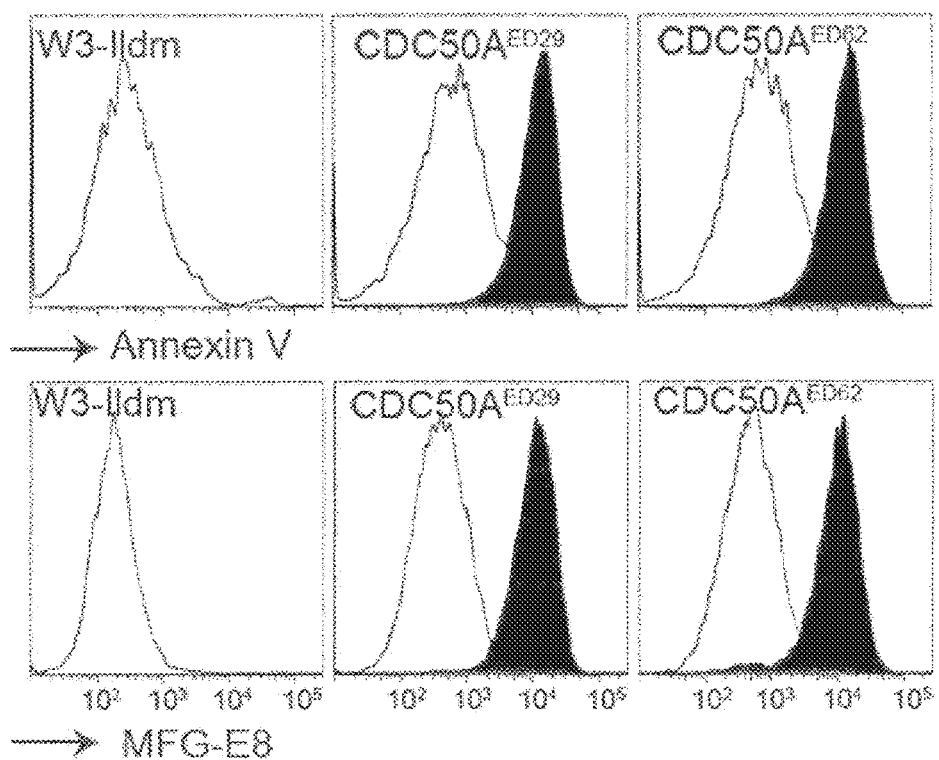
FIG. 5D Constitutive PtdSer exposure in viable CDC50A$^{-/-}$ cells (D). W3-Ildm, CDC50A$^{ED29}$, and CDC50A$^{ED62}$ were stained with Cy5-Annexin V or FITC-MFG-E8 in Annexin V-buffer, and analyzed by FACS. Staining profiles of CDC50A$^{ED29}$ and CDC50A$^{ED62}$ are shown in black. Shown in white are staining profiles of their hCDC50A-transformants.
Figure 10A:
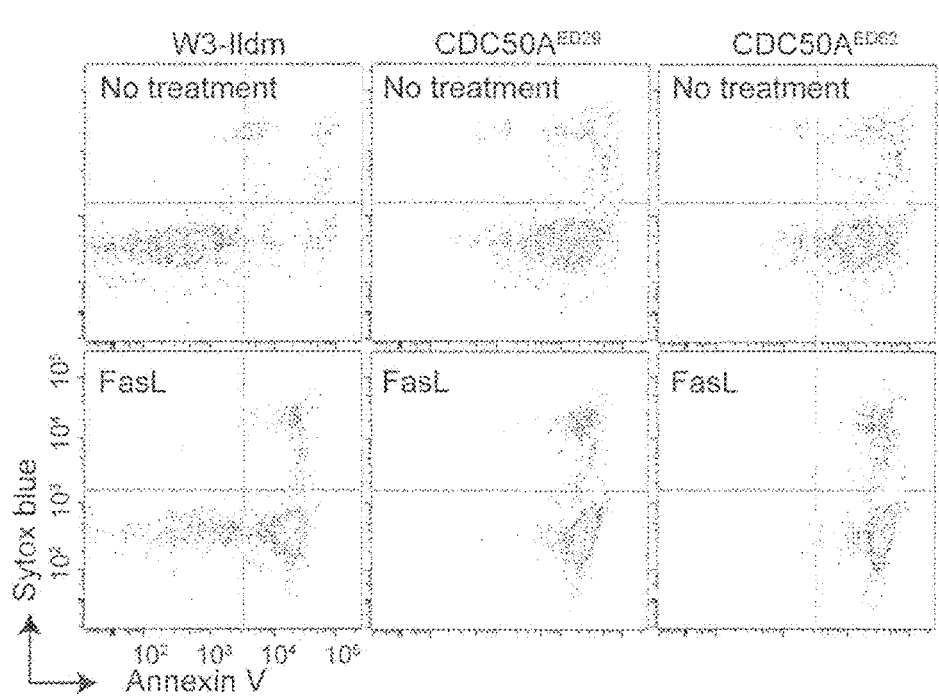
FIG. 10A PtdSer exposure in CDC50A-deficient viable cells (A). W3-Ildm, CDC50A$^{ED29}$, or CDC50A$^{ED62}$ were treated with or without FasL for 2 h, stained with Cy5-Annexin V and Sytox blue, and analyzed by flow cytometry.

Mouse CDC50A gene was then mutated using the Crispr/Cas system in W3-Ildm that expressed only CDC50A in CDC50 family (FIG. 5A). Two clones (CDC50A$^{ED29}$ and CDC50A$^{ED62}$) carried biallelic mutations in CDC50A (FIG. 5B). These mutants were defective in NBD-PS internalization (FIG. 5C) and constitutively exposed PtdSer, at a level comparable to that on apoptotic cells (FIG. 5D and FIG. 10A). Transformation of CDC50A$^{FD}$ with hCDC50A fully rescued the flippase (FIG. 5C), and blocked the PtdSer exposure (FIG. 5D).

Figure 5E:
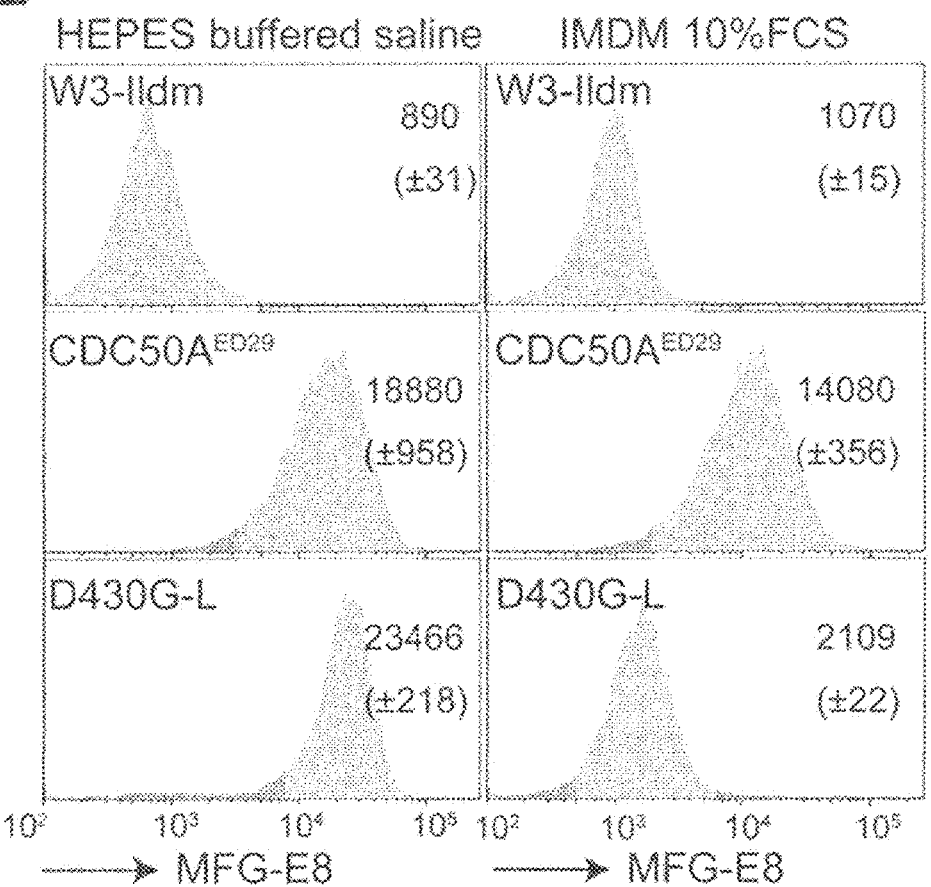
FIG. 5E Constitutive PtdSer exposure in viable CDC50A$^{-/-}$ cells (E). W3-Ildm, CDC50A$^{ED29}$, and W3-D430G-L were incubated at room temperature for 5 min with FITC-MFG-E8 in Annexin V buffer or in IMDM-10% FCS, and analyzed by FACS. MFI is indicated (n=3).
Figure 5F:
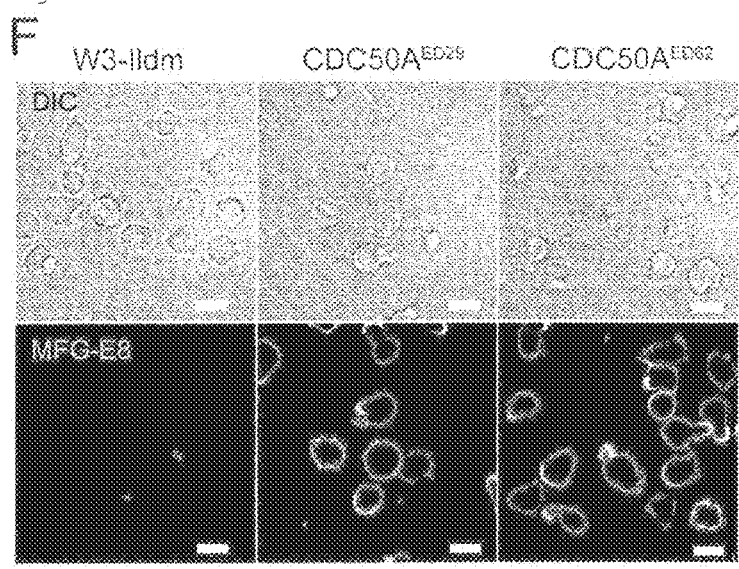
FIG. 5F Constitutive PtdSer exposure in viable CDC50A$^{-/-}$ cells (F). W3-Ildm, CDC50A$^{ED29}$, or CDC50A$^{ED62}$ were stained with FITC-MFG-E8 in IMDM-10% FCS, and observed by confocal fluorescence microscopy. Images for MFG-E8 and DIC are shown. Scale bar, 10 μm.
Figure 10B:
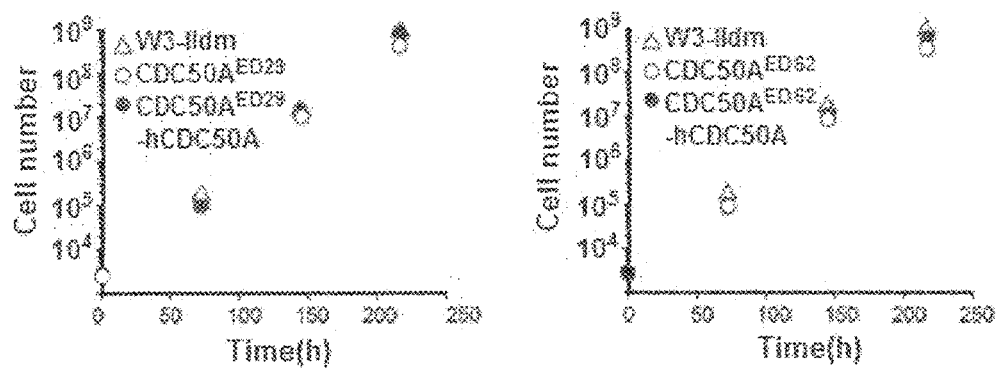
FIG. 10B PtdSer exposure in CDC50A-deficient viable cells (B). W3-Ildm, CDC50A$^{ED29}$, CDC50A$^{ED62}$, or their transformants expressing hCDC50A were seeded at $10^4$ cells/ml in RPMI containing 10% FCS, and cultured. Cells were split every 3 days, and re-seeded at $10^4$ cells/ml, and their growth was followed for 9 days.
Figure 10C:
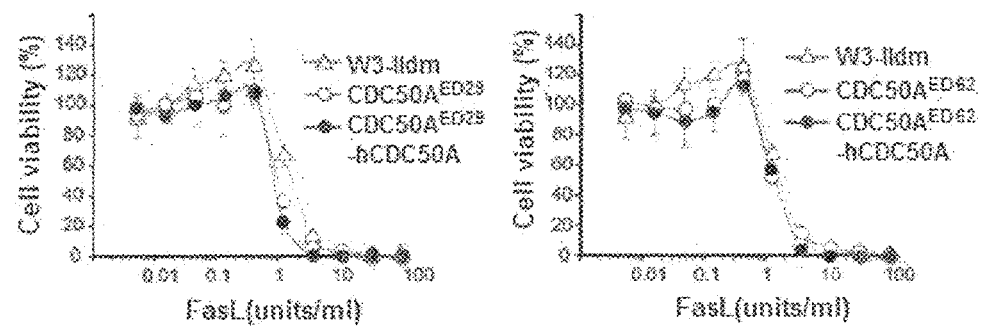
FIG. 10C PtdSer exposure in CDC50A-deficient viable cells (C). W3-Ildm, CDC50A$^{ED29}$, CDC50A$^{ED62}$, or their transformants expressing hCDC50A were incubated with the indicated concentration of FasL for 4 h at 37° C. Cell viability was determined with the WST-1 assay, and expressed as percent viability relative to viability of the cell treated in the absence of FasL.

W3 expressing a constitutively active form of TMEM16F (D430G-L) exposes high levels of PtdSer (5, 20). However, the ability of W3-D430G-L to bind MFG-E8, a PtdSer-binding protein (21), was dependent on the assay conditions. For example, these cells bound MFG-E8 in HEPES buffered saline containing 2.5 mM CaCl$_2$, but this was suppressed in IMDM containing 10% FCS (FIG. 5E). In contrast, CDC50A$^{ED}$ bound MFG-E8 even in IMDM containing 10% FCS. Observation by confocal microscope confirmed the uniform binding of MFG-E8 to CDC50A$^{ED}$ (FIG. 5F). W3-D430G-L incorporated PtdSer (FIG. 5C), suggesting that the PtdSer exposure in W3-D430G-L was regulated not only by the scramblase but also flippase. The doubling time of CDC50A$^{ED29}$ was slightly longer compared with the wild-type and the CDC50A$^{ED29}$ transformant expressing CDC50A (12.2±0.39, 13.7±0.14, and 12.4±0.13 h, respectively) (FIG. 10B). Whereas, the dose-dependency of FasL-induced apoptosis of CDC50A$^{ED}$ was similar to that observed for W3-Ildm (FIG. 10C).

PtdSer-Dependent Engulfment of Viable Cells

Figure 6A:
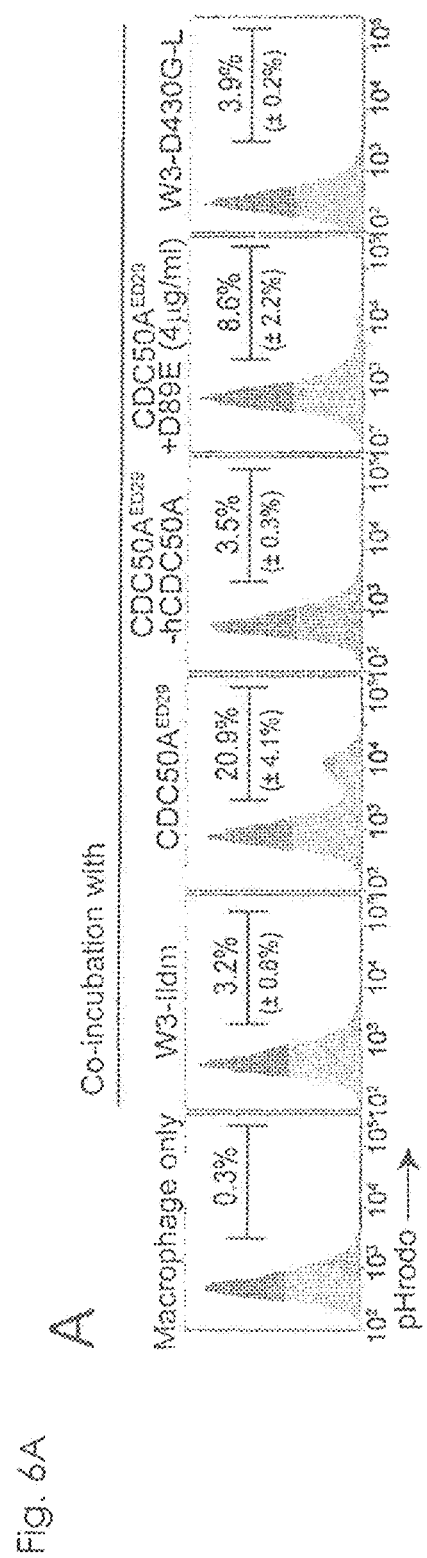
FIG. 6A Engulfment of PtdSer-exposing viable cells (A). Thio-pMacs were incubated for 2 h with pHrodo-labeled W3-Ildm, CDC50A$^{ED29}$, its hCDC50A transformant (CDC50A$^{ED29}$. hCDC50A), or W3-D430G-L in the presence or absence of 4 μg/ml of MFG-E8 D89E, and analyzed by FACS.
Figure 6B:
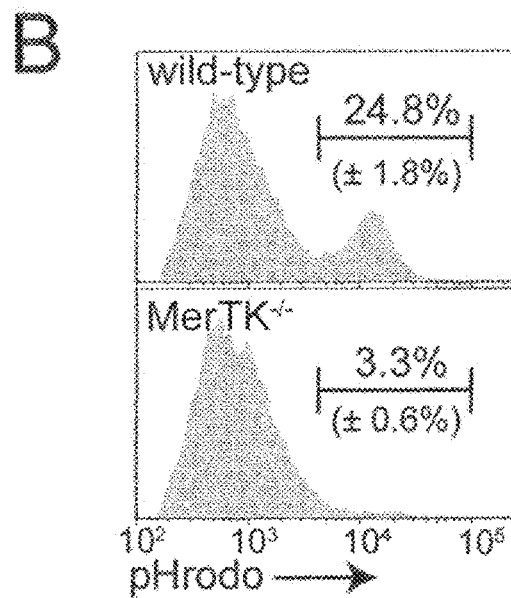
FIG. 6B Engulfment of PtdSer-exposing viable cells (B). Wild-type or MerTK$^{-/-}$ thio-pMacs were incubated for 2 h with pHrodo-labeled CDC50A$^{ED29}$, and analyzed by FACS.
Figure 6D:
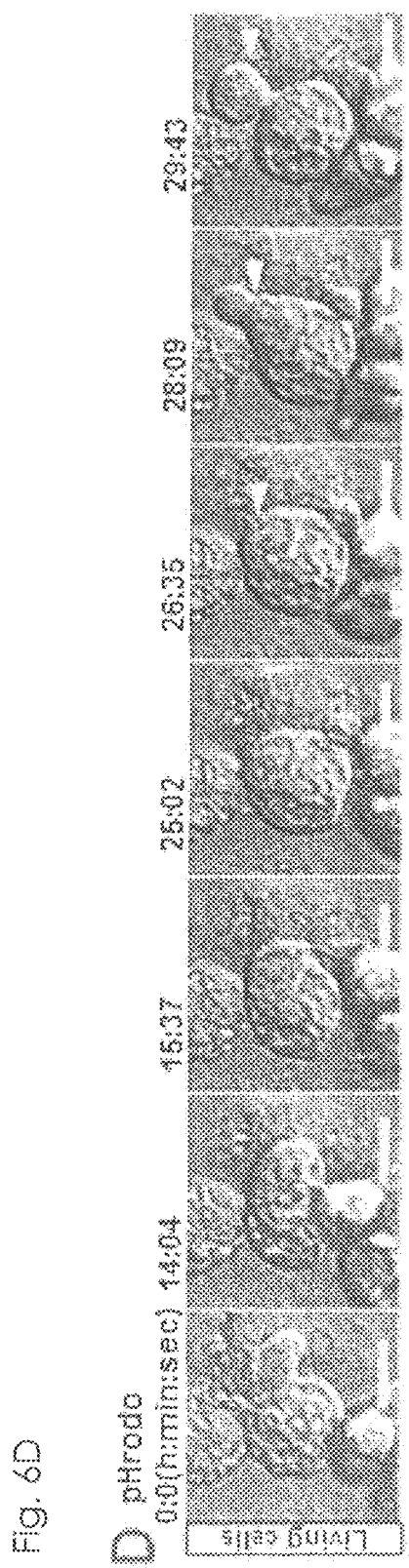
FIG. 6D Engulfment of PtdSer-exposing viable cells (D). Thio-pMacs were incubated with CDC50A$^{ED29}$. Release of engulfed cells (arrowhead) from macrophages was monitored. Scale bar, 10 μm.
Figure 6E:
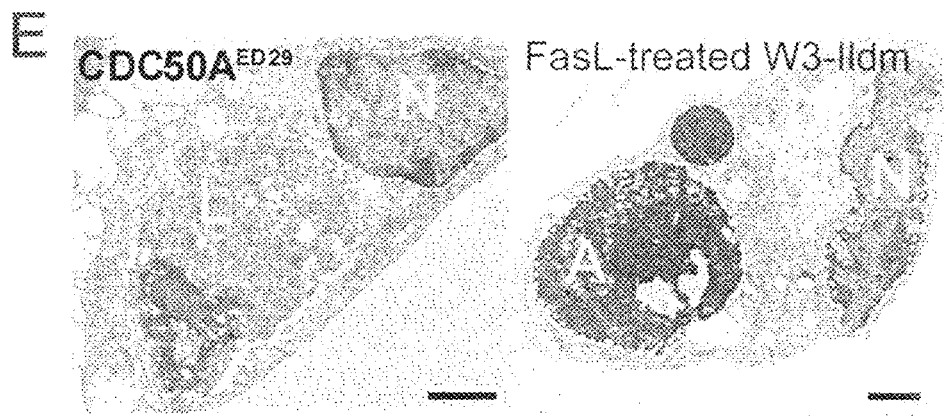
FIG. 6E Engulfment of PtdSer-exposing viable cells (E). Thio-pMacs were incubated with CDC50A$^{ED29}$ or FasL-treated W3-Ildm, and observed by electron transmission microscopy. Scale bar, 2 μm. N, macrophage nucleus. L, engulfed living cells. A, engulfed apoptotic cells.
Figure 11:
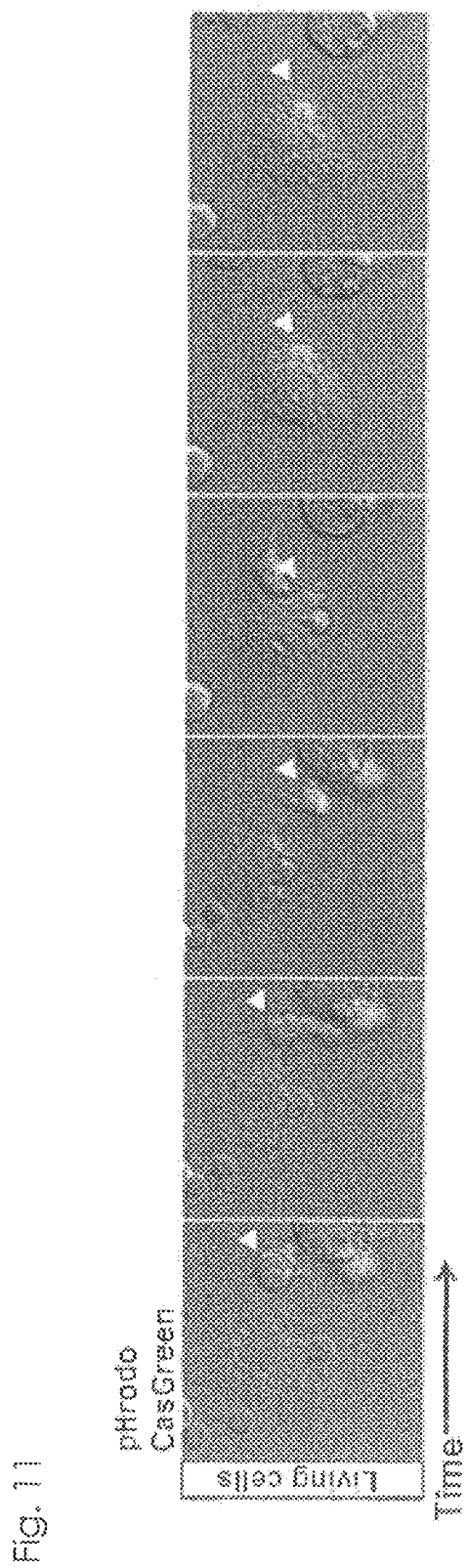
FIG. 11 Thio-pMac engulfment of PtdSer-exposing human KBM7 cells. Thio-pMacs were incubated with pHrodo-KBM7 in the presence of CellEvent™ Caspase 3/7 Green. The engulfment of KBM7 by the macrophages was followed by confocal microscope.

When pHrodo-labeled living CDC50A$^{FD}$ were co-cultured with thio-pMacs in medium containing 1.0% methylcellulose, more than 20% of the macrophages engulfed CDC50A$^{FD}$ (FIG. 6A). The thio-pMacs did not engulf W3-Ildm, W3-D430G-L, or CDC50A$^{ED}$ transformants expressing hCDC50A. The engulfment of CDC50A$^{ED29}$ was inhibited by D89E mutant of MFG-E8, which masks PtdSer (21), confirming that this process was PtdSer-dependent. MER, a tyrosine-kinase receptor, is essential for the engulfment of apoptotic cells by thio-pMacs (22). Similarly, the living CDC50A$^{ED}$ were not engulfed by MerTK$^{-/-}$ thio-pMacs (FIG. 6B). CellEvent™ caspase 3/7 green was added to cultures to mark apoptotic cells, and engulfment was monitored by time-lapse microscopy (FIG. 6C). The living cells that were not stained with CellEvent™ were frequently engulfed by macrophages and transferred to lysosomes, as indicated by their strong pHrodo-positivity. Less than 10% of cells had undergone apoptosis as indicated by the CellEvent™-staining, and were engulfed by macrophages. By monitoring 132 engulfment events, we found that approximately 80% of the engulfed cells were living, while 20% were apoptotic cells. As reported for the anoikis-induced entosis of epithelial cells (23), the engulfment of living CDC50A$^{ED}$ appeared to be reversible until a certain point. Approximately 3% of the engulfed cells were released from the macrophages before they emitted a strong pHrodo signal (FIG. 6D). The release of engulfed cells was not observed with caspase-positive ones. Examination with electron microscopy showed that the engulfed living cells had a swollen morphology (FIG. 6E), very different from the engulfed FasL-treated apoptotic cells that showed a condensed morphology. Similarly, engulfment of living PtdSer-exposing cells by thio-pMacs was observed with CDC50A-null KBM7 cells (FIG. 11).

Figure 6F:
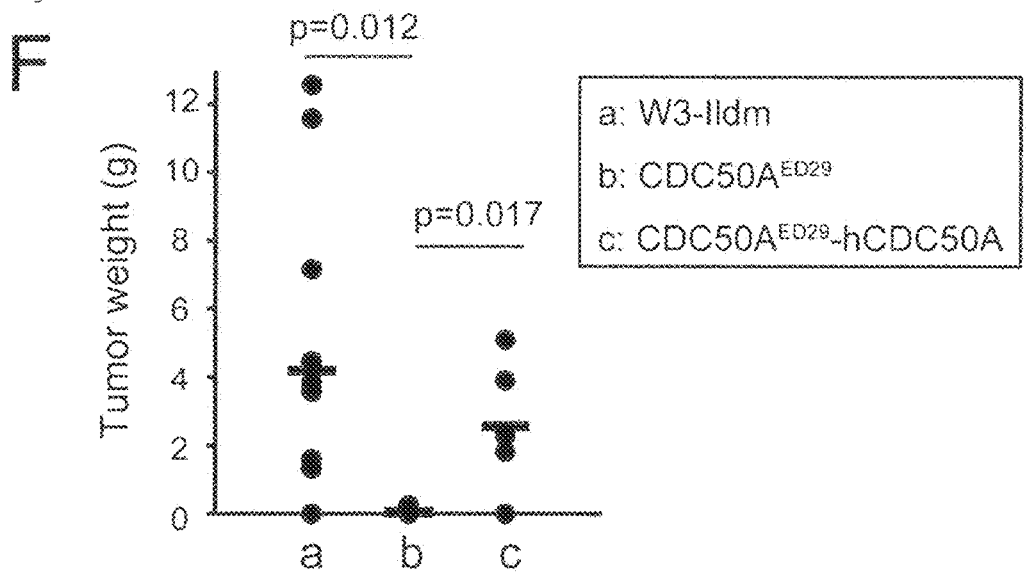
FIG. 6F Engulfment of PtdSer-exposing viable cells (F). W3-Ildm, CDC50A$^{ED29}$, and CDC50A$^{ED29}$-hCDC50A ($1 \times 10^6$ cells) were transplanted subcutaneously into nude mice (N=6-11). Four weeks later, tumors were dissected and their weights were plotted.

Subcutaneous transplantation of W3-Ildm into nude mice induced tumors in 8 of 11 recipients, and the average tumor size was approximately 4.3 g after 4 weeks (FIG. 6F). In contrast, transplanted CDC50A$^{ED}$ induced tumors in one of 6 mice, in which a small tumor (0.25 g) developed after 4 weeks. When CDC50A$^{ED}$ transformants expressing hCDC50A were transplanted into nude mice, 5 of 6 recipients developed tumors with an average size of 2.5 g. These results suggest that PtdSer-exposing CDC50A$^{ED}$ was cleared in vivo.

References (Incorporated Herein by Reference):
1. P. A. Leventis, S. Grinstein, The distribution and function of phosphatidylserine in cellular membranes. Annu. Rev. Biophys. 39, 407-427 (2010). doi:10.1146/annurev.biophys.093008.131234
2. B. Lentz, Exposure of platelet membrane phosphatidylserine regulates blood coagulation. Prog. Lipid Res. 42, 423-438 (2003). doi:10.1016/j.bbr.2011.03.031
3. S. Nagata, R. Hanayama, K. Kawane, Autoimmunity and the clearance of dead cells. Cell 140, 619-630 (2010). doi:10.1016/j.cell.2010.02.014
4. J. Suzuki et al., Xk-related protein 8 and CED-8 promote phosphatidylserine exposure in apoptotic cells. Science 341, 403-406 (2013). doi:10.1126/science.1236758
5. J. Suzuki, M. Umeda, P. J. Sims, S. Nagata, Calcium-dependent phospholipid scrambling by TMEM16F. Nature 468, 834-838 (2010). doi:10.1038/nature09583
6. P. Williamson et al., Transbilayer phospholipid movements in ABCA1-deficient cells. PLoS ONE 2, e729 (2007). doi:10.1371/journal.pone.0000729
7. K. Tanaka, K. Fujimura-Kamada, T. Yamamoto, Functions of phospholipid flippases. J. Biochem. 149, 131-143 (2011). doi:10.1093/jb/mvq140
8. T. Pomorski et al., Drs2p-related P-type ATPases Dnf1p and Dnf2p are required for phospholipid translocation across the yeast plasma membrane and serve a role in endocytosis. Mol. Biol. Cell 14, 1240-1254 (2003). doi:10.1091/mbc.E02-08-0501
9. X. Tang, M. S. Halleck, R. A. Schlegel, P. Williamson, A subfamily of P-type ATPases with aminophospholipid transporting activity. Science 272, 1495-1497 (1996).
10. O. M. Siggs, B. Schnabl, R. Webb, B. Beutler, X-linked cholestasis in mouse due to mutations of the P4-ATPase ATP11C. Proc. Nat. Acad. Sci. USA 108, 7890-7895 (2011). doi:10.1073/pnas.1104631108
11. M. Yabas et al., ATP11C is critical for the internalization of phosphatidylserine and differentiation of B lymphocytes. Nat. Immunol. 12, 441-449 (2011). doi:10.1038/ni.2011
12. V. A. van der Mark, R. P. Elferink, C. C. Paulusma, P4 ATPases: Flippases in Health and Disease. Int. J. Mol. Sci. 14, 7897-7922 (2013). doi:10.3390/ijms14047897
13. T. T. Sebastian, R. D. Baldridge, P. Xu, T. R. Graham, Phospholipid flippases: building asymmetric membranes and transport vesicles. Biochimi. Biophys. Acta 1821, 1068-1077 (2012). doi:10.1016/j.bbalip.2011.12.007
14. B. Verhoven, R. A. Schlegel, P. Williamson, Mechanisms of phosphatidylserine exposure, a phagocyte recognition signal, on apoptotic T lymphocytes. J. Exp. Med. 182, 1597-1601 (1995).
15. D. L. Bratton et al., Appearance of phosphatidylserine on apoptotic cells requires calcium-mediated nonspecific flip-flop and is enhanced by loss of the aminophospholipid translocase. J. Biol. Chem. 272, 26159-26165 (1997). doi:10.1074/jbc.272.42.26159
16. M. Kotecki, P. S. Reddy, B. H. Cochran, Isolation and characterization of a near-haploid human cell line. Exp. Cell Res. 252, 273-280 (1999). doi:10.1006/excr.1999.4656
17. J. E. Carette et al., Global gene disruption in human cells to assign genes to phenotypes by deep sequencing. Nat. Biotechnol. 29, 542-546 (2011). doi:10.1038/nbt.1857
18. J. A. Coleman, F. Quazi, R. S. Molday, Mammalian P4-ATPases and ABC transporters and their role in phospholipid transport. BBA—Mol. Cell Biol. L. 1831, 555-574 (2013). doi:10.1016/j.bbalip.2012.10.006
19. L. Cong et al., Multiplex Genome Engineering Using CRISPR/Cas Systems. Science 339, 819-823 (2013). doi:10.1126/science.1231143
20. K. Segawa, J. Suzuki, S. Nagata, Constitutive exposure of phosphatidylserine on viable cells. Proc. Natl. Acad. Sci. USA 108, 19246-19251 (2011). doi:10.1073/pnas.1114799108
21. R. Hanayama et al., Identification of a factor that links apoptotic cells to phagocytes. Nature 417, 182-187 (2002). doi:10.1038/417182a
22. H. M. Seitz et al., Macrophages and dendritic cells use different Axl/Mertk/Tyro3 receptors in clearance of apoptotic cells. J. Immunol. 178, 5635-5642 (2007).
23. M. Overholtzer et al., A nonapoptotic cell death process, entosis, that occurs by cell-incell invasion. Cell 131, 966-979 (2007). doi:10.1016/j.cell.2007.10.040
24. M. G. Palmgren, P. Nissen, P-type ATPases. Annu. Rev. Biophys. 40, 243-266 (2011). doi:10.1146/annurev.biophys.093008.131331
25. M. Auland, B. Roufogalis, P. Devaux, A. Zachowski, Reconstitution of ATP-dependent aminophospholipid translocation in proteoliposomes. Proc. Natl. Acad. Sci. USA 91, 10938-10942 (1994).

26. M. Darland-Ransom et al., Role of *C. elegans* TAT-1 protein in maintaining plasma membrane phosphatidylserine asymmetry. Science 320, 528-531 (2008). doi:10.1126/science.1155847
27. U. Kato et al., Role for phospholipid flippase complex of ATP8A1 and CDC50A proteins in cell migration. J. Biol. Chem. 288, 4922-4934 (2013). doi:10.1074/jbc.M112.402701
28. A. Siegmund et al., Loss of Drs2p does not abolish transfer of fluorescence-labeled phospholipids across the plasma membrane of *Saccharomyces cerevisiae*. J. Biol. Chem. 273, 34399-34405 (1998). doi:10.1074/jbc.273.51.34399
29. U. Marx et al., Rapid transbilayer movement of fluorescent phospholipid analogues in the plasma membrane of endocytosis-deficient yeast cells does not require the Drs2 protein. Eur. J. Biochem. 263, 254-263 (1999). doi:10.1046/j.1432-1327.1999.00497.x
30. B. Chen et al., Endocytic sorting and recycling require membrane phosphatidylserine asymmetry maintained by TAT-1/CHAT-1. PLoS Genet 6, e1001235 (2010). doi:10.1371/journal.pgen.1001235
31. A.-F. Ruaud et al., The *C. elegans* P4-ATPase TAT-1 regulates lysosome biogenesis and endocytosis. Traffic 10, 88-100 (2009). doi:10.1111/j.1600-0854.2008.00844.x
32. L. M. van der Velden et al., Heteromeric interactions required for abundance and subcellular localization of human CDC50 proteins and class 1 P4-ATPases. J. Biol. Chem. 285, 40088-40096 (2010). doi:10.1074/jbc.M110.139006
33. G. Lenoir, P. Williamson, C. F. Puts, J. C. M. Holthuis, Cdc50p plays a vital role in the ATPase reaction cycle of the putative aminophospholipid transporter Drs2p. J. Biol. Chem. 284, 17956-17967 (2009). doi:10.1074/jbc.M109.013722
34. A. Zachowski, Phospholipids in animal eukaryotic membranes: transverse asymmetry and movement. Biochem. J. 294, 1-14 (1993).
35. J. I. Elliott et al., Membrane phosphatidylserine distribution as a non-apoptotic signalling mechanism in lymphocytes. Nat. Cell Biol. 7, 808-816 (2005). doi:10.1038/ncb1279
36. D. L. Daleke, J. V. Lyles, Identification and purification of aminophospholipid flippases. Biochim. Biophys. Acta 1486, 108-127 (2000).
37. P. A. Oldenborg et al., Role of CD47 as a marker of self on red blood cells. Science 288, 2051-2054 (2000). doi:10.1126/science.288.5473.2051
38. J. J. Neher et al., Inhibition of microglial phagocytosis is sufficient to prevent inflammatory neuronal death. J. Immunol. 186, 4973-4983 (2011). doi:10.4049/jimmunol.1003600
39. G. C. Brown, J. J. Neher, Eaten alive! Cell death by primary phagocytosis: 'phagoptosis'. Trends Biochem Sci 37, 325-332 (2012). doi:10.1016/j.tibs.2012.05.002
40. C. Toyoshima, G. Inesi, Structural basis of ion pumping by Ca2+-ATPase of the sarcoplasmic reticulum. Annu Rev Biochem 73, 269-292 (2004). doi:10.1146/annurev.biochem.73.011303.073700
41. Q. Lu et al., Tyro-3 family receptors are essential regulators of mammalian spermatogenesis. Nature 398, 723-728 (1999). doi:10.1038/19554
42. R. Watanabe-Fukunaga et al., Lymphoproliferation disorder in mice explained by defects in Fas antigen that mediates apoptosis. Nature 356, 314-317 (1992).
43. H. Sakahira, M. Enari, S. Nagata, Cleavage of CAD inhibitor in CAD activation and DNA degradation during apoptosis. Nature 391, 96-99 (1998).
44. T. Kitamura, New experimental approaches in retrovirus-mediated expression screening. Int. J. Hematol. 67, 351-359 (1998)
45. T. Shiraishi et al., Increased cytotoxicity of soluble Fas ligand by fusing isoleucine zipper motif. Biochem. Biophys. Res. Commun. 322, 197-202 (2004). doi:10.1016/j.bbrc.2004.07.098
46. J. Carette et al., Haploid genetic screens in human cells identify host factors used by pathogens. Science 326, 1231-1235 (2009).
47. M. A. Nesbit et al., X-linked hypoparathyroidism region on Xq27 is evolutionarily conserved with regions on 3q26 and 13q34 and contains a novel P-type ATPase. Genomics 84, 1060-1070 (2004). doi:10.1016/j.ygeno.2004.08.003
48. R. Higuchi, in PCR protocols: A guide to methods and applications. (Academic Press, San Diego, 1990), pp. 177-188.
49. R. Fukunaga, E. Ishizaka-Ikeda, S. Nagata, Purification and characterization of the receptor for murine granulocyte colony-stimulating factor. J. Biol. Chem. 265, 14008-14015 (1990).
50. M. Miksa et al., A novel method to determine the engulfment of apoptotic cells by macrophages using pHrodo succinimidyl ester. J. Immunol. Methods 342, 71-77 (2009).
51. S. Toda, R. Hanayama, S. Nagata, Two-step engulfment of apoptotic cells. Mol. Cell. Biol. 32, 118-125 (2012). doi:10.1128/MCB.05993-11
52. H. Takatsu et al., ATP9B, a P4-ATPase (a Putative Aminophospholipid Translocase), Localizes to the trans-Golgi Network in a CDC50 Protein-independent Manner. J. Biol. Chem. 286, 38159-38167 (2011). doi:10.1074/jbc.M111.281006

Sequence Listing Free Text

SEQ ID NO: 1: amino acid sequence at position 317-334 of mATP11C
SEQ ID NO: 2: primer
SEQ ID NO: 3: primer
SEQ ID NO: 4: primer
SEQ ID NO: 5: primer
SEQ ID NO: 6: primer
SEQ ID NO: 7: primer
SEQ ID NO: 8: complementary oligonucleotide
SEQ ID NO: 9: complementary oligonucleotide
SEQ ID NO: 10: complementary oligonucleotide
SEQ ID NO: 11: complementary oligonucleotide
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 24: primer
SEQ ID NO: 25: primer
SEQ ID NO: 26: primer
SEQ ID NO: 27: primer SEQ ID NO: 28: primer
SEQ ID NO: 29: primer
SEQ ID NO: 30: primer
SEQ ID NO: 31: primer
SEQ ID NO: 32: primer
SEQ ID NO: 33: primer
SEQ ID NO: 34: primer
SEQ ID NO: 35: primer
SEQ ID NO: 36: primer
SEQ ID NO: 37: primer
SEQ ID NO: 38: primer
SEQ ID NO: 39: primer
SEQ ID NO: 40: primer
SEQ ID NO: 41: primer
SEQ ID NO: 42: primer
SEQ ID NO: 43: primer
SEQ ID NO: 44: primer
SEQ ID NO: 45: caspase-recognition sequence
SEQ ID NO: 46: caspase-recognition sequence
SEQ ID NO: 47: caspase-recognition sequence
SEQ ID NO: 48: mutated caspase-recognition sequence
SEQ ID NO: 49: mutated caspase-recognition sequence
SEQ ID NO: 50: mutated caspase-recognition sequence

---

The invention claimed is:

1. A method for screening an inhibitor of ATP11C or CDC50A, comprising:
   (a) treating tumor cells that have been transfected with an ATP11C gene and a CDC50A gene and express ATP11C and CDC50A with a candidate for said inhibitor, and
   (b) determining engulfment of the tumor cells by macrophages,
   wherein the candidate is selected as an inhibitor of ATP11C or CDC50A when the engulfment of the tumor cells by macrophages is increased by the treatment with the candidate compared to a control.

2. The method according to claim 1, which is for screening an agent for the treatment of a cancer or an apoptosis-related disease.

3. The method according to claim 2, wherein said apoptosis-related disease is an autoimmune disease.

* * * * *

SEQUENCE LISTING

<160> NUMBER OF SEQ ID NOS: 50

<210> SEQ ID NO 1
<211> LENGTH: 18
<212> TYPE: PRT
<213> ORGANISM: Artificial Sequence
<220> FEATURE:
<223> OTHER INFORMATION: Amino acid sequence at position 317-334 of
      mATP11C

<400> SEQUENCE: 1

Pro Tyr Asn Asp Glu Pro Trp Tyr Asn Gln Lys Thr Gln Lys Glu Arg
1               5                   10                  15

Glu Thr

<210> SEQ ID NO 2
<211> LENGTH: 52
<212> TYPE: DNA
<213> ORGANISM: Artificial Sequence
<220> FEATURE:
<223> OTHER INFORMATION: Primer

<400> SEQUENCE: 2
aatgatacgg cgaccaccga gatctacaca tctgatggtt ctctagcttg cc            52

<210> SEQ ID NO 3
<211> LENGTH: 45
<212> TYPE: DNA
<213> ORGANISM: Artificial Sequence
<220> FEATURE:
<223> OTHER INFORMATION: Primer

<400> SEQUENCE: 3
caagcagaag acggcatacg agatacccag gttaagatca aggtc                    45

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
ctagcttgcc aaacctacag gtggggtctt tca                                 33

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

-continued ctgcagcatc gttctgtgtt                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tctccaaatc tcggtggaac                                              20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ctcggtggaa cctccaaat                                               19

<210> SEQ ID NO 8
<211> LENGTH: 36
<212> TYPE: DNA
<213> ORGANISM: Artificial Sequence
<220> FEATURE:
<223> OTHER INFORMATION: Complementary oligonucleotide

<400> SEQUENCE: 8
aaaccatcgg cctcatcttc atccccatcg gcatgt                            36

<210> SEQ ID NO 9
<211> LENGTH: 36
<212> TYPE: DNA
<213> ORGANISM: Artificial Sequence
<220> FEATURE:
<223> OTHER INFORMATION: Complementary oligonucleotide

<400> SEQUENCE: 9
taaaacatgc cgatggggat gaagatgagg ccgatg                            36

<210> SEQ ID NO 10
<211> LENGTH: 25
<212> TYPE: DNA
<213> ORGANISM: Artificial Sequence
<220> FEATURE:
<223> OTHER INFORMATION: Complementary oligonucleotide

<400> SEQUENCE: 10
caccgtcacc aaacggttga gggtc                                        25

<210> SEQ ID NO 11
<211> LENGTH: 25
<212> TYPE: DNA
<213> ORGANISM: Artificial Sequence
<220> FEATURE:
<223> OTHER INFORMATION: Complementary oligonucleotide

<400> SEQUENCE: 11
aaacgaccct caaccgtttg gtgac                                        25

<210> SEQ ID NO 12
<211> LENGTH: 19
<212> TYPE: DNA

```
<213> ORGANISM: Artificial Sequence
<220> FEATURE:
<223> OTHER INFORMATION: Primer

<400> SEQUENCE: 12
cgtctcctaa agacgcccg                                                        19

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tccacccgac attctagctg                                                       20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gcagtgtgtt ttgtggacgg                                                       20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ccgggtttcc gctaaaacgc                                                       20

<210> SEQ ID NO 16
<211> LENGTH: 12
<212> TYPE: DNA
<213> ORGANISM: Artificial Sequence
<220> FEATURE:
<223> OTHER INFORMATION: Primer

<400> SEQUENCE: 16
cttagatgag ac                                                               12

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tggcaatcat ccagtttcgg                                                       20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
acactgtgcg tgtgccaac                                                        19
```

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
cggaaacaga agcttacatt gc                                          22

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tcgtttctct tctccagcac                                             20

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
catttaatta agccaccatg ttcag                                       25

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ccaggaattc cagcacgttg gactc                                       25

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
ctgtctggct caggccggcc acttcctggg tcacg                             35

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
cgtgacccag gaagtggccg gcctgagcca gacag                             35

<210> SEQ ID NO 25
<211> LENGTH: 35
<212> TYPE: DNA
<213> ORGANISM: Artificial Sequence
<220> FEATURE:

<223> OTHER INFORMATION: Primer

<400> SEQUENCE: 25
gaagtaggtc agtgtgccag ctgtctggct caggc        35

<210> SEQ ID NO 26
<211> LENGTH: 35
<212> TYPE: DNA
<213> ORGANISM: Artificial Sequence
<220> FEATURE:
<223> OTHER INFORMATION: Primer

<400> SEQUENCE: 26
gcctgagcca gacagctggc acactgacct acttc        35

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
ctctgtggcg ccggccacgg cggcgttggt cttga        35

<210> SEQ ID NO 28
<211> LENGTH: 35
<212> TYPE: DNA
<213> ORGANISM: Artificial Sequence
<220> FEATURE:
<223> OTHER INFORMATION: Primer

<400> SEQUENCE: 28
tcaagaccaa cgccgccgtg gccggcgcca cagag        35

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
cgatggcgat gaactataac gc        22

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
cggtataatc aatctcgatc tc        22

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ggaacgtaat gcaatggatg gg        22

-continued

```
<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
ggttagttct aagagctcag tg                                               22

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gcatcctcac cctgaagtac                                                  20

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
cttaatgtca cgcacgattt c                                                21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tgccaacagc atgtttaatg a                                                21

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ttcgaggctc tcttttccag                                                  20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
aacgactcct tctcgctctg                                                  20

<210> SEQ ID NO 38
<211> LENGTH: 20
<212> TYPE: DNA
<213> ORGANISM: Artificial Sequence
<220> FEATURE:
<223> OTHER INFORMATION: Primer
```

```
<400> SEQUENCE: 38
cacgaagtcc tggttgatga                                          20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tttcggaatc caagatccag                                          20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
cagtcggcgg tacagttttt                                          20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
ttacagttgg ggcccttctt                                          20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tatccaaggc gagcttcaga                                          20

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tgtgatggtg ggaatgggtc ag                                       22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
tttgatgtca cgcacgattt cc                                       22

<210> SEQ ID NO 45
<211> LENGTH: 5
```

```
<212> TYPE: PRT
<213> ORGANISM: Artificial Sequence
<220> FEATURE:
<223> OTHER INFORMATION: Caspase-recognition sequence

<400> SEQUENCE: 45

Gln Glu Val Asp Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Caspase-recognition sequence

<400> SEQUENCE: 46

Ser Gln Thr Asp Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Caspase-recognition sequence

<400> SEQUENCE: 47

Asp Ala Val Asp Gly
1               5

<210> SEQ ID NO 48
<211> LENGTH: 5
<212> TYPE: PRT
<213> ORGANISM: Artificial Sequence
<220> FEATURE:
<223> OTHER INFORMATION: Mutated caspase-recognition sequence

<400> SEQUENCE: 48

Gln Glu Val Ala Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Mutated caspase-recognition sequence

<400> SEQUENCE: 49

Ser Gln Thr Ala Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Mutated caspase-recognition sequence

<400> SEQUENCE: 50

Ala Ala Val Ala Gly
1               5
```